(12) United States Patent
Lee

(10) Patent No.: US 10,067,114 B2
(45) Date of Patent: Sep. 4, 2018

(54) METHOD OF RESOLVING CONTRIBUTION RATIO TO SOIL CONTAMINATION BY PLURALITY OF POLLUTERS THROUGH SEQUENTIAL EXTRACTION SCHEME AND STABLE ISOTOPE ANALYSIS SCHEME

(71) Applicant: KOREA INSTITUTE OF GEOSCIENCE AND MINERAL RESOURCES, Daejeon (KR)

(72) Inventor: Pyeong-Koo Lee, Daejeon (KR)

(73) Assignee: KOREA INSTITUTE OF GEOSCIENCE AND MINERAL RESOURCE, Daejeon (KR)

( * ) Notice: Subject to any disclaimer, the term of this patent is extended or adjusted under 35 U.S.C. 154(b) by 161 days.

(21) Appl. No.: 14/979,978

(22) Filed: Dec. 28, 2015

(65) Prior Publication Data

US 2016/0187312 A1      Jun. 30, 2016

(30) Foreign Application Priority Data

Dec. 30, 2014   (KR) .................. 10-2014-0193756

(51) Int. Cl.
    *G01N 33/00*     (2006.01)
    *G01N 33/20*     (2006.01)
    *G01N 33/24*     (2006.01)

(52) U.S. Cl.
    CPC ............. *G01N 33/20* (2013.01); *G01N 33/24* (2013.01)

(58) Field of Classification Search
    CPC ....................................... G01N 33/20
    USPC .......................................................... 436/73
    See application file for complete search history.

(56) References Cited

FOREIGN PATENT DOCUMENTS

KR      10-1349306      1/2014

OTHER PUBLICATIONS

Sequential Extraction Procedure, Jun. 1, 2010, by Pradeep Divvela http://www.caslab.com/News/sequential-extraction.html.*
Xiangdong Li, Barry J. Coles, Michael H. Ramsey, Iain Thornton "Sequential extraction of soils for multielement analysis by ICP-AES" Chemical Geology 124 (1995) 109-123.*
S.C. Wong, X.D. Lia, G. Zhang, S.H. Qi, Y.S. Min "Heavy metals in agricultural soils of the Pearl River Delta, South China" Environmental Pollution 119 (2002) 33-44.*

(Continued)

*Primary Examiner* — Christine T Mui
*Assistant Examiner* — Emily R. Berkeley
(74) *Attorney, Agent, or Firm* — Lewis Roca Rothgerber Christie LLP

(57) ABSTRACT

In a method of resolving a contribution ratio to soil contamination by a plurality of polluters through a sequential extraction scheme and a stable isotope analysis scheme, Pb stable isotopes are eluted at 5 types of "cation exchange fraction", "carbonate fraction", "iron-oxide and manganese hydroxide-fraction", "organic matters and sulfide fraction", and "residual fraction" existing at other types and separated from each other in each step. The Pb stable isotopes obtained in each step are analyzed. The contribution ratio to soil contamination by the polluters is resolved through a predetermined resolving equation using the content of a Pb stable isotope in each step based on the content ratio of the Pb stable isotopes. The Pb stable isotopes are $^{206}Pb$ and $^{207}Pb$.

1 Claim, 2 Drawing Sheets

(56) References Cited

OTHER PUBLICATIONS

Choi et al., "Distribution and Sources of Pb in Southern East/Japan Sea Sediments using Pb isotopes," Economic and Environmental Geology, vol. 39, No. 1, pp. 63-74, 2006.
Choi et al., "Source Identification of Anthropogenic Pb in Ulleung Basin Sediments using Stable Pb Isotope Ratios, East/Japan Sea," The Sea, Journal of the Korean Society of Oceanography, vol. 12, No. 4, pp. 315-327 (Nov. 2007).
Suh et al., "The Distribution Characteristics and Contamination of Heavy Metals in Soil from Dalcheon Mine," Journal of the Mineralogical Society of Korea, vol. 21, No. 1, pp. 57-65, Mar. 2008.

\* cited by examiner

METHOD OF RESOLVING CONTRIBUTION RATIO TO SOIL CONTAMINATION BY PLURALITY OF POLLUTERS THROUGH SEQUENTIAL EXTRACTION SCHEME AND STABLE ISOTOPE ANALYSIS SCHEME

CROSS-REFERENCE TO RELATED APPLICATION

This application claims the benefit of Korean Patent Application No. 10-2014-0193756, filed on Dec. 30, 2014 in the Korean Intellectual Property Office, the entirety of which is incorporated herein by reference.

BACKGROUND OF THE INVENTION

1. Field of the Invention

The present invention relates to a method of analyzing contribution ratios to soil contamination by a plurality of pollution sources adversely affecting a natural environment, especially, soil when the pollution sources multiply exist. More particularly, the present invention relates to a method of determining resolving mutual contribution ratios to soil contamination by a plurality of heavy-metal pollution sources, which multiply exist, after employing a sequential extraction scheme and a stable isotope analysis scheme in order to exactly analyze and detect various heavy-metal pollution sources harmful to a natural environment and a human body.

2. Description of the Related Art

Soil has been gone through a normal weathering process as one of natural phenomena.

During the weathering process, a mass of rock is broken into fine pieces to form a portion of the soil which is generally called a sedimentary layer.

The soil deposited as described above may contain ingredients, that is, elements, advantageous to nature, an environment, or a human body, whereas the deposited soil may contain toxic components, especially, metallic components almost existing in the form of heavy metal.

In order to exactly detect origins, that is, sources of the toxic heavy metal components, various technologies have been suggested conventionally.

Hereinafter, the conventional technologies will be described with reference to the contents of patent documents among cited references.

Meanwhile, an industrial revolution is progressed since 18C, and a huge amount of heavy metal is discharged into a natural environment as a result of the industrial revolution.

In addition, a large amount of metallic resources containing heavy metals have been mined in order to support the industrial revolution, industrially used, and wasted.

In this case, the wasted results of the industrial activities pollute the natural environment. When a mine is abandoned, the abandoned mine has continuously released the toxic heavy metals, thereby causing environment pollution.

Accordingly, it is necessary to determine the polluters or an environmental pollution source by exactly detecting the source of the heavy metals released from the abandoned mine when the heavy metals are spread due to the weathering in a natural state.

Meanwhile, the Republic of Korea (Korea) is affected by Asian dust (AD) from China seasonally throughout the winter and spring. The AD from China is mixed with other pollution sources occurring as results of industrial activities in China and moved into Korea and Japan.

The AD and pollution substances resulting from the industrial activity frequently tend to cross the boundary between nations to move a long distance. Accordingly, the AD and the pollution substances serve as broad pollution sources between nations to cause conflicts between related nations. Accordingly, each related nation makes an effort to detect the exact heavy metal pollution source.

Recently, among attempts to detect the heavy metal pollution source, studies and researches have been extensively carried out regarding the technology of determining the heavy metal pollution source using isotopes of lead (Pb).

In this case, the Pb exists as isotopes of $^{204}Pb$, $^{206}Pb$, $^{207}Pb$, and $^{208}Pb$ in a natural state. Among them, only $^{204}Pb$ is Pb stabilized since the creation of earth, and remaining isotopes are generally known as radiogenic isotopes created through the radioactive decay of $^{238}U$, $^{235}U$ and $^{232}Th$.

In general, Pb rarely contains uranium (U) or Th (thorium). Accordingly, it may be assumed that, when the Pb pollution source is created, the content (initial value) of U or Th is substantially maintained without change.

Therefore, if the content of Pb isotopes contained in the Pb pollution source is traced, the origins of the Pb pollution sources may be investigated.

In detail, when a soil (including sedimentary layers) is formed, a soil mixed through a weathering process of several grounds instead of a soil formed through the weathering process of the ground having the same origin may be estimated to represent a value varied depending on the mixture ratio. Similarly, even if a Pb isotope resulting from the activity of a human being, that is, the industrial activity is added to the soil formed through the weathering process of a pure single ground, the content of the Pb isotope, which is finally analyzed, represents a mixed value of the content of the Pb isotope derived from the pure single ground and the content the Pb isotope derived from an anthropogenic pollution source according to the content ratios of the Pb isotopes as disclosed in patent document 1.

In other words, the Pb isotopes having various origins are expected to represent the difference in the content between mutually different Pb isotopes according to the content ratios of the Pb isotopes when comparing with the content of the Pb isotope formed from the pure single ground.

In particular, soils or sedimentary layers formed through the weathering process for the single ground is estimated to have the substantially same origin in the state that different pollution sources are not mixed with the soils or the sedimentary layers, even if Pbs existing in the soils or the sedimentary layers have physically or chemically different forms. However, in the case of Pb stable isotopes contained in samples obtained by mixing the Pb stable isotopes derived from various pollution sources having mutually different origins, each origin of the Pb stable isotopes may not be exactly detected.

Accordingly, in patent document 1 (Korea Patent Registration No. 10-1349306 (Jan. 9, 2014) entitled "Method for resolving sources of heavy metal contaminants by sequential extraction scheme and isotope analysis), the content of the Pb stable isotope is analyzed in every step through a plurality of chemical treatment processes, and the contents of the Pb stable isotopes of the soil formed from the pure single ground and the contents of the Pb stable isotopes from pollution sources having mutually different origins may be distinguished.

In addition, in the case of a soil, which is weathered from the ground subject to only the same petrologic evolution process, even if chemical treatment is repeated regardless of the types of Pb existing in the soil, samples are estimated to have equal contents of Pb stable isotopes according to the types of the Pb stable isotopes existing in the samples.

Therefore, in the case of soils formed through the weathering process for several grounds subject to different petrologic evolution processes, or soils having anthropogenic Pb pollutions resulting from the industrial activities, the difference between the contents of Pb stable isotopes according to the types of the Pb stable isotopes existing in the soils is expected to be made. In consideration with the above background, patent document 1 discloses a method of analyzing contents of Pb stable isotopes formed from the pure single ground, and analyzing the contents of Pb stable isotopes derived from pollution sources having various origins to analyze the origins of the pollution sources.

Meanwhile, up to now, in order to analyze Pb isotopes in an environmental pollution analysis field, a total content analysis scheme, which is known as a full decomposition analysis scheme, has been used The full decomposition analysis scheme is to analyze whole samples including a soil polluted with heavy metal, deposits, dust, and non-Asian dust (NAD). In other words, the full decomposition analysis scheme is to chemically analyze the whole samples to be analyzed in the pretreatment of the samples.

However, as disclosed in Patent document 1, the total content analysis scheme does not reflect the characteristics, such as a mineral characteristic, the content of the organic matters, and physical and chemical characteristics, of a specific Pb isotope existing in the samples in relation to the content of Pb existing in a sample to be analyzed.

The whole Pb content in the sample has been analyzed, and the characteristic of the Pb isotope has been detected by using the analysis result without the determination if the Pb isotope is derived from an elastic mineral such as a primary mineral, a secondary mineral, or a tertiary mineral, or without distinguishing between the secondary mineral and the tertiary mineral serving as an anthropogenic pollution source of the Pb isotope resulting from the activity of a human being. Accordingly, when the content of the Pb isotope is analyzed with respect to the sample treated through the total content analysis scheme, the primary mineral, the secondary mineral, and the tertiary mineral and the Pb fractioned from the above minerals may be randomly mixed with each other. Therefore, the Pb isotope is analyzed in each step in the mixed state with the minerals without the effective separation of the pollution minerals, so that the exact analysis of the origin of the Pb isotope in the mixed state is difficult as generally known to those skilled in the art.

According to the patent document 1, the content of heavy metal, in detail, a Pb stable isotope is measured by simultaneously performing a sequential extraction scheme and an isotope analysis scheme, and the origin of a Pb pollution source including the Pb stable isotope is exactly analyzed based on the content of the Pb stable isotope.

However, the patent document 1 discloses only the configuration to specify the Pb pollution source, that is, the origin of the Pb pollution source, and does not disclose the contribution ratio to soil contamination by each pollution source when the soil contamination is caused by a plurality of polluters.

Although non-patent document 1 (Suh Ji-Won, Yoon Hye-On, and Jeong Chan-Ho, "The Distribution Characteristics and Contamination of Heavy Metals in Soil from Dalcheon Mine" in Journal of the Mineralogical Society of Korea, Vol. 21, No. 1, p. 57-65, March, 2008) among cited references employs a sequential extraction scheme to detect the type of heavy metal existing in a soil and the pollution degree of the soil by the heavy metal, only the configuration to detect the content of toxic heavy metal contained in the soil is disclosed.

Further, although non-patent document 2 (Choi Man-Sik, Cheong Chang-Sik, Han Jeong-Hee, and Park Kye-Hun, "Distribution and Sources of Pb in Southern East/Japan Sea Sediments using Pb isotopes", Economic and Environmental Geology, Vol. 39, No. 1, p. 63-74, 2006) employs the Pb isotope in order to investigate the origins of the Pb existing in the deposits, non-patent document 2 discloses the configuration for the total content analysis scheme to put a sample in HCl and $HNO_3$ solution and elute the sample.

SUMMARY OF THE INVENTION

One object of the present invention is to provide a method of exactly specifying a pollution source of heavy metal harmful to a human body.

Another object of the present invention is to exactly specify an anthropogenic pollution source of a Pb isotope resulting from the industrial activity of a human being.

The objects of the present invention are not limited to the above-mentioned object(s), and other object(s) will be clearly understood by those skilled in the art.

In order to accomplish the above objects, there are a method of resolving a contribution ratio to soil contamination by a plurality of polluters through a sequential extraction scheme and a stable isotope analysis scheme. The method includes performing the sequential extraction scheme (S100), and applying an equation of resolving the contribution ratio to the soil contamination to an analysis value of a stable isotope obtained through the sequential extraction scheme (S200).

Preferably, the performing of the sequential extraction scheme (S100) includes (A) preparing a first sample containing a Pb stable isotope, (B) preparing a first solution of 1M $MgCl_2$, pH=7, introducing the first sample into the first solution, and stirring the first sample at a normal temperature for one hour to obtain a second solution, and recovering a second sample which is the first sample remaining without being dissolved, (C) preparing a third solution of 1M $CH_3COONa$, adjusting acidity (pH) of the third solution to 5 using HOAc, introducing the second sample into the third solution, and stirring the second sample at a normal temperature for five hours to obtain a fourth solution, and recovering a third sample which is the second sample remaining without being dissolved, (D) preparing a fifth solution of 0.04M $NH_2OH.HCl$ and 25% HOAc, adjusting acidity (pH) of the fifth solution to 2, introducing the third sample into the fifth solution, and heating the third sample at a temperature of 96° C. for six hours to obtain a sixth solution, and recovering a fourth sample which is the third sample remaining without being dissolved, (E) preparing a seventh solution of 30% $H_2O_2$ and 0.02M $HNO_3$, introducing the fourth sample into the seventh solution, cooling the fourth sample at a temperature of 85° C. for five hours, additionally introducing an eighth solution of 3.2M $NH_4OAc$ and 20% $HNO_3$ into the seventh solution, and performing stirring at a normal temperature for 30 minutes to obtain a ninth solution, and recovering a fifth sample which is the fourth sample remaining without being dissolved, (F) introducing the fifth sample into a tenth solution of HF and $HClO_4$, completely drying the fifth sample through evaporation at a temperature of 110° C., introducing a 12M HCl solution, and performing heating for 30 minutes to completely dissolve the fifth sample and to obtain an eleventh solution, and (G) analyzing contents of Pb stable isotopes contained in Pb stable isotope eluates of the second, fourth, sixth, ninth, and eleventh solutions obtained in steps (B) to (F).

In this case, preferably, the Pb stable isotopes used in step (G) of analyzing the contents of the Pb stable isotopes are $^{206}$Pb and $^{207}$Pb.

In addition, $^{206}$Pb/$^{207}$Pb values measured from the second, fourth, sixth, and ninth solutions may be anthropogenic Pb stable isotope values resulting from a human activity.

Alternatively, a $^{206}$Pb/$^{207}$Pb value measured from the eleventh solution may be a geogenic Pb stable isotope value resulting from a natural activity.

Further, in the applying of the equation of resolving the contribution ratio (S200), the anthropogenic Pb stable isotope values may be obtained through following Equation, $$(^{206}Pb/^{207}Pb)_{Anthr.} = \frac{[C_{meas} \times (^{206}Pb/^{207}Pb)_{meas}] - [C_{back} \times (^{206}Pb/^{207}Pb)_{back}]}{C_{meas} - C_{back}}$$ Equation in which $(^{206}Pb/^{207}Pb)_{meas}$ denotes a Pb stable isotope value of an analyte, $(^{206}Pb/^{207}Pb)_{back}$ denotes a geogenic (natural) Pb stable isotope value, $C_{meas}$ denotes a content of Pb contained in the analyte to be measured, and $C_{back}$ denotes a content of geogenic (natural) Pb.

In addition, the contribution ratio may be resolved and specified with respect to anthropogenic and geogenic pollutions from following Equation using the above Equation, $$Pb(\%)_{anthr.} = \frac{(^{206}Pb/^{207}Pb)_{geogenic} - (^{206}Pb/^{207}Pb)_{sample}}{(^{206}Pb/^{207}Pb)_{geogenic} - (^{206}Pb/^{207}Pb)_{anthr.}} \times 100$$ Equation in which Pb (%)$_{anthr.}$ denotes the contribution ratio to the soil contamination by anthropogenic pollution, $(^{206}Pb/^{207}Pb)_{geogenic}$ denotes a Pb stable isotope value by geogenic pollution, $(^{206}Pb/^{207}Pb)_{anthr.}$ denotes a Pb stable isotope value by anthropogenic pollution, and $(^{206}Pb/^{207}Pb)_{sample}$ denotes a Pb stable isotope value of an analyte to be researched.

The details of other embodiments are included in the following description and accompanying drawings.

The advantages, the features, and schemes of achieving the advantages and features of the present invention will be apparently comprehended by those skilled in the art based on the embodiments, which are detailed later in detail, together with accompanying drawings.

The present invention is not limited to the following embodiments but includes various applications and modifications. The embodiments will make the present invention of the present invention complete, and allow those skilled in the art to completely comprehend the scope of the present invention. The present invention is only defined within the scope of accompanying claims.

Those skilled in the art should comprehend that the same reference numerals will be assigned to the same elements in the following description, and the sizes, the positions, and the coupling relationship of components will be partially exaggerated for clarity.

As described above, the origin of the Pb pollution source cannot but be exactly analyzed, but the method of resolving the contribution ratio to soil contamination by a plurality of polluters of a plurality of pollution sources can be provided by simultaneously performing the sequential extraction scheme and the isotope analysis scheme.

In other words, according to the present invention, the contribution ratios to soil contamination by a geogenic pollution source and an anthropogenic pollution source resulting from the industrial activity of a human being can be resolved and specified.

Furthermore, according to the present invention, the contribution ratios to the soil contamination by anthropogenic pollution sources resulting from various industrial activities of a human being can be resolved and specified.

DETAILED DESCRIPTION OF THE INVENTION

Hereinafter, a method of resolving the contribution ratio to the soil contamination caused by a plurality of polluters through a sequential extraction scheme and a stable isotope analysis scheme according to an exemplary embodiment of the present invention will be described with reference to accompanying drawings.

Figure 1:
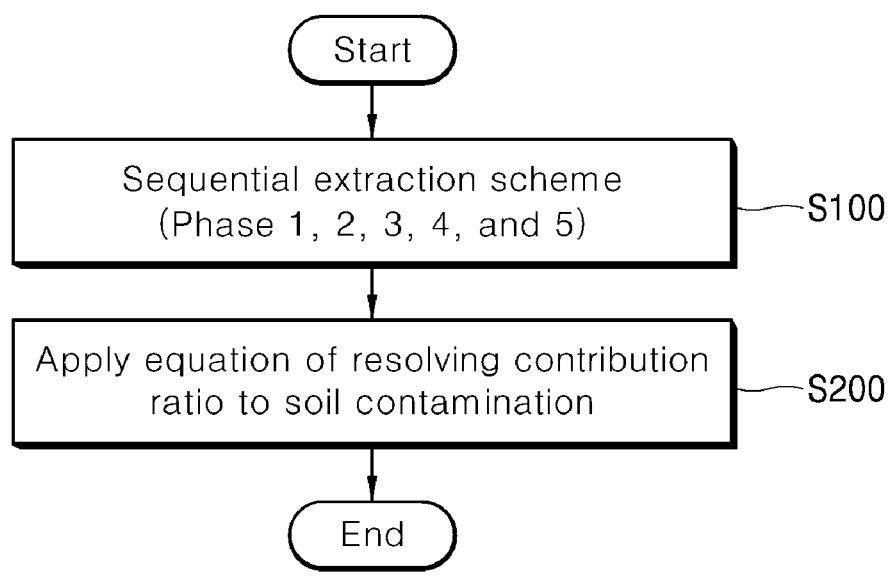
FIG. 1 is a flowchart schematically showing the sequence of a method of resolving the contribution ratio to the soil contamination by a plurality of polluters through a sequential extraction scheme and a stable isotope analysis scheme according to an exemplary embodiment of the present invention.

FIG. 1 is a flowchart schematically showing the sequence of the method of resolving the contribution ratio to the soil contamination by a plurality of polluters through the sequential extraction scheme and the stable isotope analysis scheme according to an exemplary embodiment of the present invention.

As shown in FIG. 1, the method according to the present invention includes step S100 of performing the sequential extraction scheme (phase 1, 2, 3, 4, and 5) and step S200 of applying an equation of resolving the contribution ratio to the soil contamination.

Hereinafter, the step S100 of performing the sequential extraction scheme (phase 1, 2, 3, 4, and 5) will be described with reference to FIG. 2.

Figure 2:
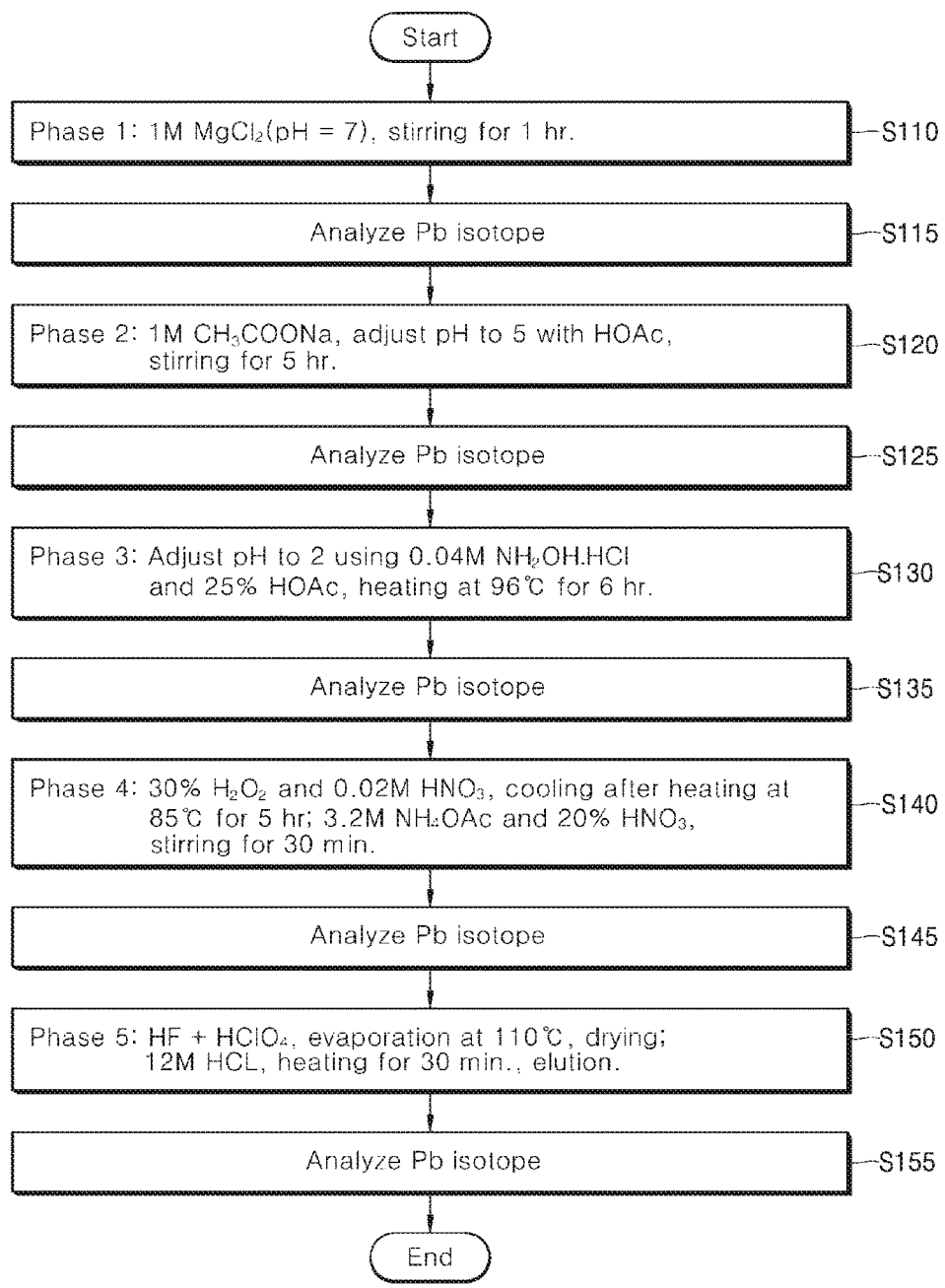
FIG. 2 is a detailed flowchart showing a sequential extraction scheme in the method of resolving the contribution ratio to the soil contamination by a plurality of polluters through the sequential extraction scheme and a stable isotope analysis scheme according to an exemplary embodiment of the present invention.

FIG. 2 is a detailed flowchart showing a sequential extraction scheme in the method of resolving the contribution ratio to the soil contamination by a plurality of polluters through the sequential extraction scheme and the stable isotope analysis scheme according to an exemplary embodiment of the present invention.

Hereinafter, the sequential extraction scheme shown in FIG. 2 and including the preparation of a sample will be described in sequence.

1. Preparation of Sample

Samples include Asian dust (AD) or non-Asian dust (NAD) called fine dust or atmospheric dust.

The samples may include all or one of the AD and the NAD. The sample is collected by installing a sample collecting tray formed of stainless steel on the rooftop of a second laboratory in Korea Institute of Geoscience and Mineral Resources. In addition, comparison samples to be compared to the samples are separately prepared.

For example, the separately prepared comparison samples may include the NAD called the fine dust in the atmosphere of the Alashan desert, various coals, or a sample obtainable from a lead mine in the People's Republic of China (China).

The samples are prepared to resolve and specify the contribution ratios to soil contamination by various pollutants from China which primarily and significantly affect Korea.

The above-described samples are provided for the illustrative purpose according to the exemplary embodiment of the present invention.

Alternatively, the samples may include various industrial wastes including Pb or coal-based materials including briquettes, which still extensively have used, discharged from various industrial sites in Korea.

Alternatively, the samples may include various samples obtainable from nations, for example, the United States, or Canada, other than Korea.

If necessary, in order to resolve the contribution ratio to seabed soil contamination and to specify a seabed soil contamination source, the samples may be obtained.

In addition, the samples need to be samples, which are not polluted by external environments, basically. If the content of a Pb stable isotope is obtained from the samples which are not polluted, it may be expected that the content of the Pb stable isotope may be actually employed as a standard.

The use of the content of the Pb stable isotope is advantageous not only to the comparison with the content of a Pb stable isotope contained in AD and NAD collected in Korea, but also to the detection of the pollution source of the samples, that is, to the specification of the pollution type of the heavy metal even when the samples are highly likely to be polluted by other pollution sources.

2. Extraction of Pb Stable Isotope Through Sequential Extraction Scheme

A Pb stable isotope was extracted from each sample, which was prepared, in each step through a sequential extraction scheme which is a chemical pre-treatment scheme.

The details of the sequential extraction scheme for the Pb stable isotope in each step will be described later in the section of "4. Sequential Extraction Scheme".

3. Analysis of Content of Pb Stable Isotope Extracted Through Sequential Extraction Scheme The content of the Pb stable isotope extracted through the sequential extraction scheme and contained in a Pb stable isotope eluate was measured.

The analysis of the content of the Pb stable isotope was performed by asking Korea Basic Science Institute, and the technical description of the analysis of the content of the Pb stable isotope will be omitted hereinafter since the technical description is out of the scope of the present invention.

4. Sequential Extraction Scheme

Hereinafter, the sequential extraction scheme according to an exemplary embodiment of the present invention will be described with reference to FIG. 2.

FIG. 2 is a flowchart showing the schematic sequence of the method of analyzing a heavy metal polluter through the sequential extraction scheme and the stable isotope analysis scheme.

As shown in FIG. 2, the sequential extraction scheme includes step S110 of obtaining a second solution by using sample 1 containing a Pb stable isotope, in detail, by preparing a first solution of 1M $MgCl_2$, pH=7, introducing the sample 1 into the first solution, and stirring the mixture at a normal temperature for one hour, step S120 of obtaining a fourth solution by preparing a third solution of 1M $CH_3COONa$, adjusting pH of the third solution to 5 using HOAc, introducing sample 2, which is prepared by recovering the sample 1 remaining without being dissolved in step S110, into the third solution, and stirring the mixture at a normal temperature for five hours, step S130 of obtaining a sixth solution by preparing a fifth solution of 0.04M $NH_2OH.HCl$ and 25% HOAc, adjusting pH of the fifth solution to 2, introducing sample 3, which is prepared by recovering the sample 2 remaining without being dissolved in the step S120, into the fifth solution, and heating the fifth solution at the temperature of 96° C. for sixth hours, step S140 of obtaining a ninth solution by preparing a seventh solution of 30% $H_2O_2$ and 0.02M $HNO_3$, introducing sample 4, which is prepared by recovering the sample 3 remaining without being dissolved in step S130, into the seventh solution, heating the seventh solution at the temperature of 85° C. for five hours and cooling, adding an eight solution of 3.2M $NH_4OAc+20\%$ $HNO_3$ to the seventh solution, and stirring the solution at the normal temperature for 30 minutes, and step S150 of obtaining an eleventh solution by introducing sample 5, which is prepared by recovering the sample 4 remaining without being dissolved in step S140, into a tenth solution of HF and $HClO_4$, completely evaporating and drying the tenth solution at the temperature of 110° C., and adding 12 M HCl solution into the tenth solution, and heating the tenth solution for 30 minutes to completely melt the sample 5.

In addition, the sequential extraction scheme further includes steps S115, S125, S135, S145, and S155 of analyzing the content of the Pb stable isotope contained in Pb stable isotope eluates of the second, fourth, sixth, ninth, and eleventh solutions obtained in the steps S115, S125, S135, S145, and S155.

In this case, the phase 5 (S150) (and, analysis step S155) may be omitted if necessary.

The omission of the phase 5 (S150) may be preferable to easily specify an anthropogenic pollution source resulting from human industrial activity.

Meanwhile, Pb isotopes are eluted at 5 types of "cation exchange fraction", "carbonate fraction", "iron-oxide and manganese hydroxide-fraction", "organic matters and sulfide fraction", and "residual fraction" existing at other types (mainly, silicate-mineral types) in phases 1 to 5 (S110 to S150), and a sample is partially eluted sequentially in each step to form each fraction type.

For reference, phases 1 to 5 described above may be designated as first to five phases, or FI, FII, FIII, FIV, and FV. Hereinafter, those skilled in the art should understand that the phases 1 to 5 (first to five phases) may be described as FI to FV.

Hereinafter, the details of each of the phases 1 to 5 will be described.

4-1. Phase 1 (S110)

In phase 1 (S110), the second solution serving as a Pb stable isotope eluate is obtained by preparing the first solution of 1M $MgCl_2$, pH=7, introducing the sample 1, which is previously prepared, into the first solution, and stirring the mixture at a normal temperature for one hour.

In this case, 8 mL of first solution was prepared, and an amount of the first solution may be varied depending on an amount of the sample 1.

In this case, the second solution is the first solution used to analyze the Pb stable isotope.

Meanwhile, the sample 1 remaining in the first solution without being dissolved is separately recovered as the second sample for the use in the subsequent step.

For reference, when the sample 1 is pulverized in the particle size of 80 to 100 meshes, the sample 1 may be more easily melted.

4-2. Phase 2 (S120)

In phase 2 (S120), the fourth solution is obtained as a Pb stable isotope eluate by preparing the third solution of 1M $CH_3COONa$, adjusting pH of the third solution to 5 using HOAc, introducing the sample 2, which is prepared by recovering the sample 1 remaining without being dissolved in step S110, into the third solution, and stirring the mixture at a normal temperature for five hours.

In this case, 8 mL of third solution was prepared, and an amount of the second solution to be prepared may be varied depending on an amount of the sample 2.

In this case, the fourth solution is the second solution used to analyze the Pb stable isotope.

The sample remaining in the third solution without being dissolved is separately recovered as the third sample for the use in the subsequent step.

4-3. Phase 3 (S130)

In step S130, the sixth solution is obtained as a Pb stable isotope eluate by preparing the fifth solution of 0.04M $NH_2OH.HCl$ and 25% HOAc, adjusting pH of the fifth solution to 2, introducing the sample 3, which is prepared by recovering the sample 2 remaining without being dissolved in the step S120, into the fifth solution, and heating the fifth solution at the temperature of 96° C. for sixth hours.

In this case, 20 mL of fifth solution was prepared, and an amount of the fifth solution to be prepared may be varied depending on an amount of the sample 3.

In this case, the sixth solution is the third solution used to analyze the Pb stable isotope.

Meanwhile, the sample remaining in the third solution without being dissolved is separately recovered as the fourth sample for the use in the subsequent step.

4-4. Phase 4 (S140)

In step S140, the ninth solution is obtained as a Pb stable isotope eluate by preparing the seventh solution of 30% $H_2O_2$ and 0.02M $HNO_3$, introducing the sample 4, which is prepared by recovering the sample 3 remaining without being dissolved in step S130, into the seventh solution, heating the seventh solution at the temperature of 85 for five hours and cooling, adding the eight solution of 3.2M $NH_4OAc+20\%$ $HNO_3$ to the seventh solution, and stirring the solution at the normal temperature for 30 minutes.

In this case, 20 mL of seventh solution was prepared, and an amount of the seventh solution to be prepared may be varied depending on an amount of the sample 1.

Meanwhile, the ninth solution is the fourth solution used to analyze the Pb stable isotope.

In this case, the sample 4 remaining in the eighth solution without being dissolved is separately recovered as the sample 5 for the use in the subsequent step.

4-5. Phase 5 (S150)

In step S150, the eleventh solution is obtained as a Pb stable isotope eluate by introducing sample 5, which is prepared by recovering the sample 4 remaining without being dissolved in step S140, into the tenth solution of $HF+HClO_4$, completely evaporating and drying the tenth solution at the temperature of 110° C., and adding 12 M HCl solution into the tenth solution, heating the tenth solution for 30 minutes to completely melt the sample 5.

In this case, 25 mL of seventh solution was prepared, and an amount of the seventh solution to be prepared may be varied depending on an amount of the sample 5.

In this case, the eleventh solution is the fifth solution used to analyze the Pb stable isotope.

The steps S110 to S150 may further include steps S115, S125, S135, S145, and S155 to analyze the content of the Pb stable isotope contained in the second, fourth, sixth, ninth, and eleventh solutions serving as the Pb stable isotope eluates.

4-6 Steps S115, S125, S135, S145, and S155

Steps S115, S125, S135, S145, and S155 are to analyze the content of the Pb stable isotopes contained in the second, fourth, sixth, ninth, and eleventh solutions serving as the Pb stable isotope eluates obtained from phase 1 (S110) to phase 5 (S150), respectively.

The origin of a Pb pollution source including heavy metal, in detail, Pb stable isotope may be exactly obtained by simultaneously performing the sequential extraction scheme and the stable isotope analysis scheme. Furthermore, through step S200 of applying an equation of resolving the contamination ratio to soil contamination based on the analyzed value of the Pb stable isotope obtained through the sequential extraction scheme of FIG. 1, the contribution ratio to the soil contamination by a plurality of polluters may be resolved and specified.

Hereinafter, the step S200 of applying an equation of resolving the contamination ratio to soil contamination based on the analyzed value of the Pb stable isotope obtained through the sequential extraction scheme according to an exemplary embodiment of the present invention will be described.

Hereinafter, the description will be made in that the resolution of the contribution ratios to the soil contamination by the pollution sources is performed using a specific equation.

In addition, according to an exemplary embodiment of the present invention, the Pb stable isotopes used to analyze the contents of the Pb stable isotopes are $^{206}Pb$ and $^{207}Pb$.

In other words, $^{206}Pb$ and $^{207}Pb$, which are Pb stable isotopes, are employed since the Pb stable isotopes are advantageous when the contribution ratios to the soil contamination by a plurality of polluters are resolved.

In other words, Pb stable isotopes other than 206Pb and 207Pb are disadvantageous when the resolution of the contribution ratios by the polluters is specified.

The following equation is to find an anthropogenic Pb stable isotope.

$$(^{206}Pb/^{207}Pb)_{Anthr.} = \frac{[C_{meas} \times (^{206}Pb/^{207}Pb)_{meas}] - [C_{back} \times (^{206}Pb/^{207}Pb)_{back}]}{C_{meas} - C_{back}} \quad \text{Equation 1}$$

In Equation 1, $(^{206}Pb/^{207}Pb)_{meas}$ denotes a Pb stable isotope value of an analyte, $(^{206}Pb/^{207}Pb)_{back}$ denotes a geogenic (natural) Pb stable isotope value, $C_{meas}$ denotes a content of Pb contained in the analyte to be measured, and $C_{back}$ denotes a content of geogenic (natural) Pb.

Through Equation 1, the contribution ratios may be resolved and specified with respect to anthropogenic and geogenic pollutions from following Equation 2 when Equation 1 is used.

$$Pb(\%)_{anthr.} = \frac{\left(^{206}Pb/^{207}Pb\right)_{geogenic} - \left(^{206}Pb/^{207}Pb\right)_{sample}}{\left(^{206}Pb/^{207}Pb\right)_{geogenic} - \left(^{206}Pb/^{207}Pb\right)_{anthr.}} \times 100 \quad \text{Equation 2}$$

In Equation 2, $Pb(\%)_{anthr.}$ denotes the contribution ratio to soil contamination by anthropogenic pollution, $(^{206}Pb/^{207}Pb)_{geogenic}$ denotes a Pb stable isotope value by geogenic pollution, $(^{206}Pb/^{207}Pb)_{anthr.}$ denotes a Pb stable isotope value by anthropogenic pollution, and $(^{206}Pb/^{207}Pb)_{sample}$ denotes a Pb stable isotope value of the analyte to be researched.

The contribution ratios to soil contamination by anthropogenic and geogenic pollutions may be resolved using Equation 2. When an anthropogenic pollution source includes at least two polluters, the contribution ratio to the soil contamination by the anthropogenic pollution source may be resolved as follows.

As the simplest example, when there are two anthropogenic pollution sources, the contribution ratios to the soil pollution by the two anthropogenic pollution sources may be found using following Equation 3.

For example, when the anthropogenic pollution sources are gasoline and industrial waste, the contribution ratio may be expressed through following Equation 3.

$$Pb_{gas}(\%) = \frac{\left(^{206}Pb/^{207}Pb\right)_{indus} - \left(^{206}Pb/^{207}Pb\right)_{Anthr.}}{\left(^{206}Pb/^{207}Pb\right)_{indus} - \left(^{206}Pb/^{207}Pb\right)_{gas}} \times 100 \quad \text{Equation 3}$$

In Equation 3, when the values of $(^{206}Pb/^{207}Pb)_{indus}$ and $(^{206}Pb/^{207}Pb)_{gas}$ are found, the anthropogenic pollution source may be found from the gasoline and the industrial waste.

Meanwhile, as described below, on the assumption that the Pb pollution is derived from both of China and Korea, the contribution ratios to soil contamination by Chinese Pb pollution and Korean Pb pollution are calculated through Equations 4 and 5, so that the contribution ratios to the atmospheric pollutions may be resolved in the embodiment to be described below.

$$\left(^{206}Pb/^{207}Pb\right)_{Anthr.} = \frac{C_{Pb_{measu}} \times \left(^{206}Pb/^{207}Pb\right)_{meas} - C_{Pb_{back}} \times \left(^{206}Pb/^{207}Pb\right)_{back}}{(C_{Pb_{meas}} - C_{Pb_{back}})} \quad \text{Equation 4}$$

$$Pb_{china}(\%) = \frac{[((^{206}Pb)/(^{207}Pb))_{Korea} - ((^{206}Pb)/(^{207}Pb))_{Anthr.}] \times 100}{((^{206}Pb)/(^{207}Pb))_{Korea} - ((^{206}Pb)/(^{207}Pb))_{China}} \quad \text{Equation 5}$$

Equations 4 and 5 may be solved only when China and Korea $(^{206}Pb/^{207}Pb)$ values are given. In this case, since values for NAD contained in fine dust are generally known through various references, the references are utilized in the present invention.

Meanwhile, on the assumption that $(^{206}Pb/^{207}Pb)$ values measured in Fractions I, II, III, and IV after samples are dissolved through the sequential extraction scheme are $(^{206}Pb/^{207}Pb)$ values produced by the anthropogenic pollution, the $(^{206}Pb/^{207}Pb)$ value measured in the Fraction V may be the elemental value of geogenic (natural) $(^{206}Pb/^{207}Pb)$ lead.

The present invention will be described hereinafter while keeping in mind the above description.

For example, according to one embodiment of the present invention, the ratio of a Pb stable isotope derived from atmospheric dust in Fraction V of AD dissolved through the sequential extraction scheme is calculated through following Equation 6.

$$P_{anthr.} = \frac{[Pb]_{AD}^{FV} - [Pb]_{Desert\ Soil}^{FV}}{[Pb]_{AD}^{FV}} \quad \text{Equation 6}$$

The anthropogenic pollution ratio by the atmospheric pollution in each of Fractions I, II, III, and IV may be found in Equation 6.

Next, the $^{206}Pb/^{207}Pb$ value resulting from anthropogenic pollution in each Fraction may be found by using $^{206}Pb/^{207}Pb$ values measured in Fractions I, II, III, and IV.

For example, the way of finding a $^{206}Pb/^{207}Pb$ value, which is an anthropogenic Pb stable isotope value in Fraction II, using an isotope value and a Pb concentration measured in Fraction II, in which a desert sample is dissolved with the isotope value, the Pb concentration, and a background concentration measured in Fraction II, through the sequential extraction scheme, is expressed through following Equation 7.

$$\left(^{206}Pb/^{207}Pb\right)_{anthr.}^{FII} = \frac{\left[\left(^{206}Pb/^{207}Pb\right)_{AD}^{FII} \times C_{AD}^{FII}\right] - \left[\left(^{206}Pb/^{207}Pb\right)_{DS}^{FII} \times C_{DS}^{FII}\right]}{C_{AD}^{FII} - C_{DS}^{FII}} \quad \text{Equation 7}$$

In Equation 7, AD is an abbreviation of Asian dust, and DS is an abbreviation of Desert Soil.

The anthropogenic lead stable isotope value may be obtained using Equation 7.

The method of resolving the contribution ratios to soil contamination by the anthropogenic pollution and the geogenic pollution is performed using the result of Equation 7 as follows.

$$P_{anthr.}^{FII}(\%) = \frac{\left(^{206}Pb/^{207}Pb\right)_{DS}^{FII} - \left(^{206}Pb/^{207}Pb\right)_{sample}^{FII}}{\left(^{206}Pb/^{207}Pb\right)_{DS}^{FII} - \left(^{206}Pb/^{207}Pb\right)_{anthr.}^{FII}} \times 100 \quad \text{Equation 8}$$

In Equation 8, DS represents a geogenic Pb stable isotope value detected in Fraction II (FII) for desert soil.

In addition, anthr represents an anthropogenic Pb stable isotope value detected in FII for AD.

The above calculation may be performed through Equation 9 even in FI, FIII, FIV, or FV in the same manner.

$$P_{anthr.}(\%) = \Sigma \left( P^{FI}(\%) \times \frac{C^{FI}}{C_{TL}} + P^{FII}(\%) \times \frac{C^{FII}}{C_{TL}} + P^{FIII}(\%) \times \frac{C^{FIII}}{C_{TL}} + P^{FIV}(\%) \times \frac{C^{FIV}}{C_{TL}} + P^{FV}(\%) \times \frac{C^{FV}}{C_{TL}} \right) \quad \text{Equation 9}$$

After resolving the contribution ratio to soil contamination by an anthropogenic pollution source and the contribution ratio to soil contamination by a geogenic pollution source through Equation 9, when the anthropogenic pollution source includes at least two polluters, the resolving of the contribution ratio to the soil contamination by an anthropogenic pollution source may be performed as follows.

When two sources of pollution exist, the contribution ratio to the soil contamination by each source of pollution may be obtained through Equation 10.

For example, when the anthropogenic source of pollution includes gasoline and industrial waste, Equation 10 may be expressed as follows.

$$Pb_{gas}(\%) = \frac{(^{206}Pb/^{207}Pb)_{indus} - (^{206}Pb/^{207}Pb)_{Anthr.}}{(^{206}Pb/^{207}Pb)_{indus} - (^{206}Pb/^{207}Pb)_{gas}} \times 100 \quad \text{Equation 10}$$

In detail, when Equation 10 is employed, for example, when sediments are targets, a portion of Equation 10 may be modified as shown in Equation 11.

$$(^{206}Pb/^{207}Pb)_{leached\ residue} = \frac{[(^{206}Pb/^{207}Pb)_{total\ sed} \times C^{total\ sed}] - [(^{206}Pb/^{207}Pb)_{leached\ solution} \times C^{leached\ solution}]}{C_{leached\ residue}}$$

$$= (C_{total\ sed} - C_{leached\ solution}) \quad \text{Equation 11}$$

In Equation 11, 'leached residue' represents a Pb stable isotope value of residues after elution, and 'total sed' represents a Pb stable isotope value of sediments.

Meanwhile, it should be noted that the resolution of the contribution ratios to soil contamination by the geogenic pollution and the anthropogenic pollution is complex.

This is because soil is formed through long-term weathering for millions of years so that the variation in the contribution ratio to the soil contamination by the anthropogenic pollution with time must be reflected on the resolution of the contribution ratios to the soil contamination.

Particularly, it may be assumed that a geogenic Pb is substituted into an anthropogenic Pb with time in the geogenic silicate mineral in Fraction V (silicate mineral fraction). Accordingly, the mixture between the geogenic isotope value and the anthropogenic isotope value may be estimated according to the substitution ratio of the geogenic Pb into the anthropogenic Pb.

In addition, the geogenic Pb stable isotope value may be assumed as being substituted into the anthropogenic Pb stable isotope value in Fraction V among soil samples.

Accordingly, when the above assumptions are reflected on the resolution method, the geogenic Pb isotope value may be more exactly calculated.

Therefore, whether the geogenic Pb is substituted into the anthropogenic Pb or not may be calculated as follows.

In detail, the percentage of the anthropogenic Pb stable isotope value in Fraction V is calculated through following Equation 12.

$$P_{anthr.} = \frac{[Pb]_{silicate}^{component} - [Pb]_{pristine}^{component}}{[Pb]_{silicate}^{component}} \times 100 \quad \text{Equation 12}$$

In Equation 12, $[Pb]_{silicate}^{component}$ represents the Pb concentration in the silicate mineral per unit mass (Pb concentration in Fraction V).

In addition, $[Pb]_{pristine}^{component}$ represents the Pb concentration in silicate mineral obtained from soil that is not contaminated, that is, Pb concentration in silicate mineral at the deepest soil.

In Equation 12, the Pb concentration values are proportional to Pb concentration ($[Pb]_{silicate}^{soil}$) in the silicate mineral per unit mass of soil as expressed in following Equation 13.

$$[Pb]_{silicate}^{component} = \frac{[Pb]_{silicate}^{soil}}{f_{silicate}} \quad \text{Equation 13}$$

In Equation 13, $f_{silicate}$ represents the ratio of an amount of silicate mineral contained in the samples.

On the assumption that the variation of the Pb concentration indicates Pb concentration added to the silicate mineral, the calculation of the Pb stable isotope value may be applied to the calculation of the ratio of the anthropogenic Pb in a given sample.

In other words, if the ratio of the anthropogenic Pb calculated based on stable isotope data exceeds a ratio suggested based on Pb concentration data, the geogenic Pb is considered exchange to the anthropogenic Pb in the silicate mineral of soil.

Accordingly, the percentage of the anthropogenic Pb may be calculated through following Equation 14.

$$P_{anthr.} = \frac{(^{206}Pb/^{207}Pb)_{pristine}^{silicate} - (^{206}Pb/^{207}Pb)_{sample}^{silicate}}{(^{206}Pb/^{207}Pb)_{pristine}^{silicate} - (^{206}Pb/^{207}Pb)_{anthr.}} \times 100 \quad \text{Equation 14}$$

In Equation 14, pristine represents geogenic Pb in Fraction V, and anthr represents anthropogenic Pb in Fraction V.

In Equation 14, the ratio of an isotope in Fraction V contained in the deepest sample may be represented as $(^{206}Pb/^{207}Pb)_{pristine\ silicate}$.

The final value of $^{206}Pb/^{207}Pb$ derived from an anthropogenic pollution source may not be easily set.

However, the value at the depth having the highest Pb concentration and the lowest $^{206}Pb/^{207}Pb$, for example, the value at the upper most part of about 10 cm or less may be estimated as the final value of the anthropogenic pollution ($^{206}Pb/^{207}Pb$).

In this case, the exchange of the anthropogenic Pb in Fraction V is made through long-term reaction.

In this regard, the content of anthropogenic Pb in Fraction V may be less than the content of anthropogenic Pb in various other mineral components.

The anthropogenic $^{206}Pb/^{207}Pb$ value in Fraction V calculated in consideration of various matters is expected to have the minimum value.

The minimum value may be obtained through following Equation 15.

$$\left(^{206}Pb/^{207}Pb\right)_{sample} = \frac{(Pb)_{app.} \times (Pb^{206})_{app.} \times W_{back} + (Pb)_{back} \times (Pb^{206})_{back} \times W_{app.}}{(Pb)_{app.} \times (Pb^{207})_{app.} \times W_{back} + (Pb)_{back} \times (Pb^{207})_{back} \times W_{app.}}$$

Equation 15

In Equation 15, $(Pb)_{app.}$ represents the content of Pb added to the sample, $(Pb)_{back}$ represents the content of background Pb in the sample, $(Pb^{206})_{app.}$ and $(Pb^{207})_{app.}$ represent isotope values of $Pb^{206}$ and $Pb^{207}$ added to the sample, respectively.

$(Pb^{206})_{back}$ and $(Pb^{207})_{back}$ represent the isotope values of background $Pb^{206}$ and background $Pb^{207}$, respectively.

$(W)_{app.}$ and $(W)_{back}$ represent the atomic weights of added Pb and the background Pb, respectively.

Hereinafter, the method of resolving the contribution ratio to the soil contamination by the plural polluters through the sequential extraction scheme and the stable isotope analysis scheme will be described in more detail with reference to the following embodiments.

Embodiment

Hereinafter, the configuration and the operation of the present invention will be described according to exemplary embodiments.

The following descriptions of the embodiments are provided for illustrative purpose, and do not limited the present invention.

In other words, the matters, which are not described in the present specification, can be sufficiently and technically conceivable by those skilled in the art, so the details thereof will be omitted.

1. Preparation of Sample

As described above, the inventor of the present invention selects and prepares AD or NAD including fine dust as a representative sample moving between nations Since the AD or the NAD moves beyond Korea through mainland China after generating from inland provinces of China, the AD or the NAD is a desirable sample to investigate causes regarding whether a Pb pollution source included in the AD refers to a generation point of the AD, an anthropogenic pollution source is added to the AD due to industrial activity in the mainland China during the movement of the AD, or the AD is exposed to an anthropogenic pollution source in Korea after the AD has moved from China to Korea. The AD or the NAD may be appropriately applied to the method of resolving the contribution ratio to the soil contamination by a plurality of polluters through the analysis of the Pb stable isotope.

For example, 0.6 g of an AD sample and 0.4 g of an NAD sample were collected.

Since the AD sample and the NAD sample are fine dust in themselves, the AD sample and the NAD may not be additionally pulverized. However, when a soil sample in the form of sediment is used, the soil sample is preferably pulverized in the particle size of 80 to 100 meshes.

2. Sequential Extraction Scheme

The sequential extraction scheme has been described above, so that the details thereof will be omitted.

3 Analysis Result of Content of Pb Stable Isotope.

As described above, the analysis results of Pb stable isotopes after Pb stable isotopes has been eluted from previously prepared samples through the sequential extraction scheme including phase 1 (S110) to phase 5 (S150) as described above are summarized in tables 9 to 11, which include original data, to be described later.

For reference, data of 2007 and 2008, which are obtained by investigating and analyzing the contents of various elements contained in AD and NAD, are shown in tables 1 and 2.

TABLE 1

|  |  | As | Cd | Cu | Pb | Zn | Mo | Sb | Zr | S |
|---|---|---|---|---|---|---|---|---|---|---|
| TSP | Avg. | 105 | 13.6 | 326 | 850 | 2370 | 345 | 174 | 4670 | 86190 |
| $PM_{10}$ | Avg. | 140 | 8.7 | 440 | 957 | 1430 | 384 | 54.2 | 3020 | 38080 |
| $PM_{2.5}$ | Avg. | 892 | 26.6 | 1180 | 2890 | 5380 | 2120 | 301 | 18740 | 129030 |

TABLE 2

|  |  | As | Cd | Cu | Pb | Zn | Mo | Sb | Zr | S |
|---|---|---|---|---|---|---|---|---|---|---|
| TSP | Avg. | 64.5 | 17.0 | 344 | 783 | 2340 | 201 | 123 | 3410 | 77460 |
| $PM_{10}$ | Avg. | 219 | 16.7 | 356 | 935 | 2130 | 374 | 103 | 4430 | 76000 |
| $PM_{2.5}$ | Avg. | 290 | 44.4 | 990 | 2520 | 5490 | 1580 | 492 | 21220 | 175570 |

In tables 1 and 2, unit is ppm, and Pb concentration observed in the present invention is marked in bold.

Meanwhile, as described above, Pb concentrations required for various calculations can be obtained through various literature data in order to perform the method of resolving the contribution ratio to soil contamination by a plurality of polluters through the sequential extraction scheme and the stable isotope analysis scheme according to an exemplary embodiment of the present invention.

First, average values of AD, NAD, and other Chinese urban dust are shown in following table 3.

TABLE 3

| Area | | As | Cd | Cr | Co | Cu | Ni |
|---|---|---|---|---|---|---|---|
| Dry deposition of Asian dust, Daejeon (N = 7) | Mean | 30.2 ± 15.2 | 1.86 ± 0.69 | 81.6 ± 12.8 | 14.6 ± 1.0 | 359.1 ± 363.9 | 41.1 ± 4.5 |
| | Range | 14.0-58.9 | 0.95-2.79 | 69.3-104.8 | 13.2-15.9 | 52.6-1135 | 38.0-50.8 |
| | CV | 0.5 | 0.37 | 0.16 | 0.07 | 1.01 | 0.11 |
| Dry deposition of non-Asian dust, Daejeon (N = 8) | Mean | 77.1 ± 45.0 | 2.16 ± 0.69 | 135.3 ± 32 | 12.5 ± 2.5 | 453.5 ± 388.9 | 65.6 ± 19.0 |
| | Range | 9.2-132.9 | 0.67-2.71 | 72.4-169.4 | 8.7-16.7 | 126.6-1184 | 33.8-88.7 |
| | CV | 0.58 | 0.32 | 0.24 | 0.2 | 0.86 | 0.29 |
| Regional soil, Daejeon (N = 4) | Mean | 2.5 ± 0.4 | 0.12 ± 0.03 | 14.4 ± 1.5 | 3.3 ± 0.3 | 7.1 ± 0.6 | 6.1 ± 0.6 |
| | Range | 2.3-2.8 | 0.10-0.14 | 13.3-15.4 | 3.1-3.5 | 6.7-7.5 | 5.7-6.5 |
| | CV | 0.14 | 0.24 | 0.1 | 0.09 | 0.08 | 0.09 |
| China background values in soils [1] | Mean | | 0.1 | 61 | | 22.6 | 26.9 |
| Uncontaminated Chinese desert soils | | 6.5 ± 3.3 | 0.1 ± 0.03 | 26.9 ± 13.5 | 5.5 ± 3.3 | 12.3 ± 7.5 | 16.1 ± 9.9 |
| Urban soils in 20 Chinese cities [2] | Mean | | 1.6 | 78.4 | | 115.1 | 99.5 |
| | Range | | 0.2-8.6 | 23.1-194.7 | | 23.3-1226 | 27.8-910.3 |
| Agricultural soils in 12 Chinese cities [2] | Mean | 10.2 | 0.4 | 58.9 | | 31.7 | 27.5 |
| | Range | 6.2-14.9 | 0.1-2.6 | 22.6-87.7 | | 21.2-42.5 | 15.5-38.5 |
| Roadside sediment in Seoul, Korea [a] (N = 633) | Mean | | 4.3 ± 3.3 | 182 ± 269 | | 446 ± 708 | 89.6 ± 206 |
| | Range | | 0.0-25.7 | 0.1-3310 | | 0.2-9000 | 0.0-2390 |
| Roadside sediment, Seoul, Korea [b] (N = 30) | Mean | | 6 | 106 | | 269 | |
| | Range | | 3.8-8.4 | 47.8-257 | | 76.3-565 | |
| Street dust, Seoul, Korea [c] | Mean | | | 151 | | 396 | |
| Road dusts (Industrial/Traffic), Daejeon, Korea [d] | Mean | | | | | 47.0/57.0 | |
| Street dust, Hong Kong [e] | Mean | | | 124 ± 7.0 | | 110 ± 4.0 | 28.6 ± 5.2 |
| Urban dust in Nanjing [f] | Mean | 12.5 | | | 15.9 | 141.4 | 55.4 |
| Urban dust in Xi'an, China [g] | Mean | 10.6 | | 167.3 | | 95 | |
| | Range | 5.9-20 | | 28-853 | | 20-1071 | |
| Urban dust Xi'an, China [f] | Mean | 28.5 | | | 19.4 | 102.7 | 56.7 |
| Street dust, Lanzhou, China [h] | Mean | | | 62.14 | | 72.97 | |
| Street dust, Shanghai, China [i,j] | Mean | | | 242 | | 141 | |
| Street dust, Beijing, China [i,k] | Mean | | | 86 | | 42 | |
| Street dust, Hong Kong [i] | Mean | | | 324 | | 534 | |
| Urban road dust in 7 Chinese cities [l] | Mean | | 2.03 | 109.16 | | 149.62 | 56.75 |
| | Range | | 1.17-3.77 | 51.3-167.3 | | 94.9-196.8 | 23-86.26 |

| Area | | Pb | Zn | Zr | Mo | S |
|---|---|---|---|---|---|---|
| Dry deposition of Asian dust, Daejeon (N = 7) | Mean | 140.1 ± 58.8 | 448.4 ± 314.4 | 168.7 ± 95.7 | 5.29 ± 1.33 | 12941 ± 8559 |
| | Range | 39.2-216.0 | 124.6-1106 | 106.6-334.1 | 3.64-7.19 | 3194-25040 |
| | CV | 0.42 | 0.7 | 0.57 | 0.25 | 0.66 |
| Dry deposition of non-Asian dust, Daejeon (N = 8) | Mean | 367.9 ± 171 | 863.7 ± 254.0 | 577.0 ± 590 | 13.2 ± 7.42 | 6134 ± 2782 |
| | Range | 156.5-656.3 | 493.1-1304 | 74.3-1611 | 5.72 ± 24.6 | 2783-9750 |
| | CV | 0.47 | 0.29 | 1.02 | 0.56 | 0.45 |
| Regional soil, Daejeon (N = 4) | Mean | 20.7 ± 1.0 | 44.0 ± 1.8 | 45.8 ± 6.3 | 0.45 ± 0.10 | 91.3 ± 99.6 |
| | Range | 20.0-21.4 | 42.8-45.3 | 41.4-50.3 | 0.38-0.52 | 20.9-161.8 |
| | CV | 0.05 | 0.04 | 0.14 | 0.21 | 1.09 |
| China background values in soils [1] | Mean | 26 | 100 | | | |
| Uncontaminated Chinese desert soils | Mean | 14.7 ± 2.4 | 26.0 ± 14.4 | 139.6 ± 103 | 1.8 ± 1.7 | 214.0 ± 440.5 |
| Urban soils in 20 Chinese cities [2] | Mean | 1350.5 | 266.4 | | | |
| | Range | 28.6-25380 | 65.6-1964 | | | |
| Agricultural soils in 12 Chinese cities [2] | Mean | 37.6 | 117.7 | | | |
| | Range | 17.1-77.3 | 52.2-227.0 | | | |
| Roadside sediment in Seoul, Korea [a] (N = 633) | Mean | 214 ± 148 | 2670 ± 1820 | | | |
| | Range | 0.0-2130 | 1.1-12400 | | | |
| Roadside sediment, Seoul, Korea [b] (N = 30) | Mean | 144 | 532 | | | |
| | Range | 52.8-301 | 208-1010 | | | |
| Street dust, Seoul, Korea [c] | Mean | 144 | 795 | | | |
| Road dusts (Industrial/Traffic), Daejeon, Korea [d] | Mean | 60.0/52.0 | 172/214 | | | |
| Street dust, Hong Kong [e] | Mean | 120 ± 4.0 | 3840 ± 70.0 | | | |
| Urban dust in Nanjing [f] | Mean | 213.2 | 576 | | | |
| Urban dust in Xi'an, China [g] | Mean | 230.5 | 421.5 | | | |
| | Range | 29-3060 | 80-2112 | | | |
| Urban dust Xi'an, China [f] | Mean | 266.3 | 798 | | | |
| Street dust, Lanzhou, China [h] | Mean | 62.65 | 296.92 | | | |
| Street dust, Shanghai, China [i,j] | Mean | 148 | 699 | | | |
| Street dust, Beijing, China [i,k] | Mean | 61 | 214 | | | |
| Street dust, Hong Kong [i] | Mean | 240 | 4024 | | | |
| Urban road dust in 7 Chinese cities [l] | Mean | 238.66 | 655.94 | | | |
| | Range | 53.3-408.4 | 294.5-1450 | | | |

The data shown in table 3 may be obtained from [1]CEPA, 1990 Lee et al., 2013; [2]Wei and Yang (2010) [a]Lee et al. (2005); [b]Yun et al. (2000); [c]Kim et al. (2009) [d]Kim et al. (1998) [e]Yeung et al. (2003); [f]Cao et al. (2011) [g]Yongming et al. (2006) [h] Wang et al. (2012) [i]Tanner et al. (2008) [j]Jia. (2010) [k]Zheng and Zhang. (2008) [l]Wei and Yang. (2010).

Next, Pb concentrations (average values) for desert soil in China are shown in table 4.

TABLE 4

| Area | | As | Cd | Cr | Co | Cu | Ni |
|---|---|---|---|---|---|---|---|
| Taklamakan (N = 11) | Mean ± S.D | 4.9 ± 0.4 | 0.1 ± 0.0 | 20.9 ± 3.3 | 4.2 ± 0.5 | 10.2 ± 1.5 | 12.8 ± 1.2 |
| | Range | 4.3-5.5 | 0.05-0.11 | 16.9-29.5 | 3.6-5.4 | 8.0-13.2 | 11.4-15.4 |
| | CV | 0.08 | 0.22 | 0.16 | 0.13 | 0.15 | 0.09 |
| Loess (N = 10) | Mean ± S.D | 11.4 ± 1.6 | 0.1 ± 0.0 | 45.4 ± 6.5 | 10.6 ± 2.1 | 23.7 ± 4.3 | 29.7 ± 5.4 |
| | Range | 9.4-13.6 | 0.09-0.16 | 37.6-56.8 | 7.5-14.2 | 16.2-31.2 | 22.9-39.8 |
| | CV | 0.14 | 0.2 | 0.14 | 0.19 | 0.18 | 0.18 |
| Alashan (N = 7) | Mean ± S.D | 5.3 ± 1.7 | 0.1 ± 0.0 | 25.6 ± 15.4 | 4.2 ± 1.6 | 9.7 ± 2.4 | 16.1 ± 9.3 |
| | Range | 3.3-8.2 | 0.03-0.08 | 12.4-45.4 | 2.4-6.7 | 6.9-13.5 | 8.0-32.7 |
| | CV | 0.32 | 0.34 | 0.48 | 0.39 | 0.24 | 0.58 |
| Ordos (N = 16) | Mean ± S.D | 5.1 ± 2.7 | 0.1 ± 0.0 | 20.0 ± 11.2 | 3.6 ± 2.3 | 7.9 ± 5.5 | 9.8 ± 7.5 |
| | Range | 2.2-11.0 | 0.02-0.11 | 5.7-40.3 | 1.1-8.5 | 3.4-22.6 | 3.1-25.3 |
| | CV | 0.53 | 0.41 | 0.56 | 0.64 | 0.7 | 0.77 |
| Uncontaminated Chinese desert soils | Mean ± S.D | 6.5 ± 3.3 | 0.1 ± 0.03 | 26.9 ± 13.5 | 5.5 ± 3.3 | 12.3 ± 7.5 | 16.1 ± 9.9 |
| | Range | 2.2-13.6 | 0.02-0.16 | 5.7-56.8 | 1.1-14.2 | 3.4-31.2 | 3.1-39.8 |
| | CV | 0.5 | 0.42 | 0.5 | 0.61 | 0.6 | 0.62 |
| China background values in soils [a] | Mean | | 0.1 | 61 | | 22.6 | 26.9 |
| Urban soils in the 20 cities from china [b] | Mean | | 1.6 | 78.4 | | 115.1 | 99.5 |
| | Range | | 0.2-8.6 | 23.1-194.7 | | 23.3-1226.3 | 27.8-910.3 |
| Agricultural soils in the 12 cities from china [b] | Mean | 10.2 | 0.4 | 58.9 | | 31.7 | 27.5 |
| | Range | 6.2-14.9 | 0.1-2.6 | 22.6-87.7 | | 21.2-42.5 | 15.5-38.5 |

| Area | | Pb | Zn | Zr | Mo | S |
|---|---|---|---|---|---|---|
| Taklamakan (N = 11) | Mean ± S.D | 13.7 ± 2.1 | 23.7 ± 8.7 | 167.5 ± 167 | 2.8 ± 2.7 | 342 ± 709.5 |
| | Range | 12.1-19.1 | 15.6-43.5 | 62.2-540.5 | 1.2-8.8 | 106.5-2480.8 |
| | CV | 0.16 | 0.37 | 1 | 0.97 | 2.07 |
| Loess (N = 10) | Mean ± S.D | 17.8 ± 1.8 | 46.5 ± 8.5 | 157.3 ± 118.1 | 2.1 ± 1.8 | 192.2 ± 127.5 |
| | Range | 14.7-21.1 | 32.5-58.1 | 103.6-491.5 | 1.3-7.2 | 80-486 |
| | CV | 0.1 | 0.18 | 0.75 | 0.85 | 0.66 |
| Alashan (N = 7) | Mean ± S.D | 12.4 ± 2.0 | 19.2 ± 4.6 | 112.9 ± 38.8 | 1.3 ± 0.5 | 321.7 ± 601.2 |
| | Range | 9.6-15.4 | 13.9-25.6 | 73.6-181.5 | 0.8-2.13 | 59.0-1681.9 |
| | CV | 0.16 | 0.24 | 0.34 | 0.37 | 1.87 |
| Ordos (N = 16) | Mean ± S.D | 14.3 ± 0.9 | 17.7 ± 10.5 | 120.9 ± 41.2 | 1.1 ± 0.4 | 92.6 ± 181.6 |
| | Range | 12.2-16.0 | 7.0-43.0 | 65.2-184.5 | 0.75-1.87 | 26.8-769.8 |
| | CV | 0.06 | 0.59 | 0.34 | 0.33 | 1.96 |
| Uncontaminated Chinese desert soils | Mean ± S.D | 14.7 ± 2.4 | 26.0 ± 14.4 | 139.6 ± 103.6 | 1.8 ± 1.7 | 214.0 ± 440.5 |
| | Range | 9.6-21.1 | 7.0-58.1 | 62.2-540.5 | 0.7-8.8 | 26.8-2480.8 |
| | CV | 0.17 | 0.55 | 0.74 | 0.95 | 2.06 |
| China background values in soils [a] | Mean | 26 | 100 | | | |
| Urban soils in the 20 cities from china [b] | Mean | 1350.5 | 266.4 | | | |
| | Range | 28.6-25380.5 | 65.6-1964.1 | | | |
| Agricultural soils in the 12 cities from china [b] | Mean | 37.6 | 117.7 | | | |
| | Range | 17.1-77.3 | 52.2-227.0 | | | |

The data shown in table 4 is obtained from [a]CEPA, 1990; [b]Wei and Yang (2010).

Meanwhile, as described above, Pb concentrations required for various calculations are shown in tables 5 and 6 in order to perform the method of resolving the contribution ratio to soil contamination by a plurality of polluters through the sequential extraction scheme and the stable isotope analysis scheme according to an exemplary embodiment of the present invention.

TABLE 5

| Nationals | Regions | Sample no. | $^{208}Pb/^{204}Pb$ | $^{207}Pb/^{204}Pb$ | $^{206}Pb/^{204}Pb$ | $^{206}Pb/^{207}Pb$ | $^{208}Pb/^{206}Pb$ |
|---|---|---|---|---|---|---|---|
| Korea | Asian dust (N = 10) | F4 | 38.1191 | 15.6176 | 18.2477 | 1.1684 | 2.0889 |
| | | F13 | 38.2055 | 15.6038 | 18.1866 | 1.1656 | 2.1007 |
| | | F14 | 38.0326 | 15.5902 | 18.0778 | 1.1596 | 2.1037 |
| | | F15 | 38.1851 | 15.5828 | 18.1427 | 1.1643 | 2.1047 |
| | | F16 | 38.2485 | 15.6269 | 18.3782 | 1.1761 | 2.0811 |
| | | F17 | 38.0641 | 15.6206 | 18.3066 | 1.1720 | 2.0792 |
| | | F65-3-3 | 38.1328 | 15.5937 | 18.1367 | 1.1631 | 2.1025 |
| | | F79-3-2 | 38.1952 | 15.6189 | 18.3682 | 1.1760 | 2.0794 |
| | | F130-3-2 | 38.1635 | 15.5905 | 18.3037 | 1.1740 | 2.0850 |
| | | F131-3-4 | 37.9896 | 15.5868 | 18.1415 | 1.1639 | 2.0941 |

TABLE 5-continued

| Nationals | Regions | Sample no. | $^{208}Pb/^{204}Pb$ | $^{207}Pb/^{204}Pb$ | $^{206}Pb/^{204}Pb$ | $^{206}Pb/^{207}Pb$ | $^{208}Pb/^{206}Pb$ |
|---|---|---|---|---|---|---|---|
| | non-Asian dust (N = 12) | F3 | 37.9146 | 15.5708 | 17.8459 | 1.1460 | 2.1248 |
| | | F5 | 38.0217 | 15.5805 | 18.0236 | 1.1568 | 2.1096 |
| | | F8 | 38.2586 | 15.6210 | 18.1725 | 1.1633 | 2.1052 |
| | | F11 | 38.0599 | 15.5912 | 18.0858 | 1.1601 | 2.1042 |
| | | F12 | 38.0658 | 15.5967 | 18.1691 | 1.1649 | 2.0951 |
| | | F18 | 37.9853 | 15.5758 | 18.0012 | 1.1557 | 2.1101 |
| | | F19 | 38.0613 | 15.5939 | 18.1841 | 1.1661 | 2.0931 |
| | | F22 | 38.0618 | 15.5942 | 18.1316 | 1.1628 | 2.0991 |
| | | F27 | 38.0119 | 15.5926 | 18.0070 | 1.1549 | 2.1108 |
| | | F147-3-2 | 37.8316 | 15.5667 | 18.0199 | 1.1576 | 2.0994 |
| | | F152-3-2 | 38.1163 | 15.6063 | 18.2083 | 1.1667 | 2.0993 |
| | | F154-3-4 | 38.1129 | 15.5929 | 18.0895 | 1.1601 | 2.1068 |
| | Dry deposition of Asian dust (N = 6) | Sd-4 | 38.1100 | 15.6150 | 17.8780 | 1.1450 | 2.1317 |
| | | Sd-5-a | 37.8950 | 15.6090 | 17.8370 | 1.1427 | 2.1245 |
| | | Sd-5-b | 37.7013 | 15.5553 | 17.7656 | 1.1421 | 2.1221 |
| | | Sd-6 | 37.9517 | 15.5747 | 17.9528 | 1.1527 | 2.1138 |
| | | Sd-7 | 38.2254 | 15.5861 | 18.1940 | 1.1673 | 2.1008 |
| | | Sd-8 | 38.1158 | 15.6097 | 18.0261 | 1.1547 | 2.1145 |
| | Dry deposition of non-Asian dust (N = 7) | nsd-1 | 38.1729 | 15.6110 | 18.0503 | 1.1563 | 2.1148 |
| | | nsd-2 | 38.0965 | 15.5892 | 18.0490 | 1.1578 | 2.1107 |
| | | nsd-3 | 37.9658 | 15.5580 | 18.0022 | 1.1571 | 2.1090 |
| | | nsd-10-a | 38.1130 | 15.6090 | 17.9340 | 1.1489 | 2.1252 |
| | | nsd-18 | 37.7185 | 15.5627 | 17.8190 | 1.1449 | 2.1167 |
| | | nsd-23 | 38.3149 | 15.6386 | 18.0354 | 1.1532 | 2.1245 |
| | | nsd-25 | 38.1081 | 15.6061 | 17.9996 | 1.1534 | 2.1172 |
| | Regional soil, Daejeon (N = 5) | BG1 | 38.6203 | 15.6347 | 18.3755 | 1.1753 | 2.1016 |
| | | BG2 | 38.6027 | 15.5153 | 18.4566 | 1.1896 | 2.0915 |
| | | BG3 | 38.2409 | 15.4805 | 18.2171 | 1.1768 | 2.0991 |
| | | BS-1 | 39.2862 | 15.6783 | 18.5800 | 1.1850 | 2.1145 |
| | | BS-2 | 39.2296 | 15.6787 | 18.5708 | 1.1845 | 2.1123 |

TABLE 6

| | | | $^{208}Pb/^{204}Pb$ | $^{207}Pb/^{204}Pb$ | $^{206}Pb/^{204}Pb$ | $^{206}Pb/^{207}Pb$ | $^{208}Pb/^{206}Pb$ |
|---|---|---|---|---|---|---|---|
| China Desert soil | Loess (N = 10) | 82101 | 38.1834 | 15.4261 | 18.5980 | 1.2056 | 2.0531 |
| | | 82102 | 38.8902 | 15.6363 | 18.7347 | 1.1982 | 2.0757 |
| | | 82103 | 38.9371 | 15.6544 | 18.7794 | 1.1996 | 2.0733 |
| | | 82201 | 39.0912 | 15.6567 | 18.8507 | 1.2040 | 2.0736 |
| | | 82202 | 38.8880 | 15.6394 | 18.7588 | 1.1995 | 2.0729 |
| | | 82203 | 38.9383 | 15.6495 | 18.7717 | 1.1995 | 2.0743 |
| | | 82204-1 | 38.7140 | 15.6003 | 18.7304 | 1.2006 | 2.0669 |
| | | 82204-2 | 38.8804 | 15.6476 | 18.7273 | 1.1968 | 2.0761 |
| | | 82501 | 38.8718 | 15.6380 | 18.7626 | 1.1998 | 2.0717 |
| | | 82502 | 38.1937 | 15.4719 | 18.5814 | 1.2010 | 2.0554 |
| | Taklamakan (N = 11) | 71601 | 38.9205 | 15.6538 | 18.6681 | 1.1926 | 2.0847 |
| | | 71602 | 38.7243 | 15.6143 | 18.6018 | 1.1913 | 2.0817 |
| | | 71603 | 38.8121 | 15.6318 | 18.6160 | 1.1909 | 2.0848 |
| | | 71701 | 38.7354 | 15.6428 | 18.6599 | 1.1929 | 2.0757 |
| | | 71702 | 38.2813 | 15.5081 | 18.5394 | 1.1955 | 2.0649 |
| | | 71703 | 38.7829 | 15.6441 | 18.6397 | 1.1915 | 2.0806 |
| | | 71704 | 38.5108 | 15.5598 | 18.5719 | 1.1936 | 2.0736 |
| | | 71801 | 38.1532 | 15.4104 | 18.5318 | 1.2025 | 2.0587 |
| | | 71802 | 38.6125 | 15.5843 | 18.6505 | 1.1968 | 2.0702 |
| | | 71803 | 37.8933 | 15.3710 | 18.4292 | 1.1990 | 2.0560 |
| | | 71804 | 38.7878 | 15.6177 | 18.6641 | 1.1951 | 2.0782 |
| | Alashan (N = 6) | 112802 | 38.5511 | 15.5568 | 18.4356 | 1.1851 | 2.0911 |
| | | 112803 | 38.4897 | 15.5826 | 18.4358 | 1.1831 | 2.0877 |
| | | 112804 | 38.6463 | 15.6246 | 18.5192 | 1.1853 | 2.0868 |
| | | 112805 | 38.6448 | 15.6268 | 18.5115 | 1.1846 | 2.0876 |
| | | 112806 | 38.3755 | 15.5837 | 18.1891 | 1.1672 | 2.1098 |
| | | 112807 | 38.2134 | 15.5514 | 18.0671 | 1.1617 | 2.1151 |
| | Ordos (N = 16) | 112501 | 37.7155 | 15.44434 | 17.4646 | 1.1309 | 2.1595 |
| | | 112502 | 37.5225 | 15.4075 | 17.3507 | 1.1261 | 2.1624 |
| | | 112503 | 37.6866 | 15.4413 | 17.4970 | 1.1332 | 2.1538 |
| | | 112504 | 37.5448 | 15.4096 | 17.3981 | 1.1291 | 2.1579 |
| | | 112505 | 37.7180 | 15.44409 | 17.4594 | 1.1308 | 2.1602 |
| | | 112506 | 37.2858 | 15.3286 | 17.3267 | 1.1304 | 2.1518 |
| | | 112507 | 37.5887 | 15.4055 | 17.2883 | 1.1222 | 2.1742 |
| | | 112508 | 37.6850 | 15.4255 | 17.3028 | 1.1217 | 2.1779 |
| | | 112509 | 37.7074 | 15.4090 | 17.1853 | 1.1153 | 2.1941 |
| | | 112510 | 37.8822 | 15.2709 | 16.9844 | 1.1123 | 2.1714 |
| | | 112601 | 37.2497 | 15.3915 | 17.0935 | 1.1106 | 2.1791 |
| | | OR12 | 38.8330 | 15.6193 | 18.6924 | 1.1968 | 2.0775 |
| | | OR13 | 38.5610 | 15.5641 | 18.5700 | 1.1932 | 2.0765 |
| | | OR14 | 38.7438 | 15.6240 | 18.6844 | 1.1959 | 2.0736 |

TABLE 6-continued

| | | | | | |
|---|---|---|---|---|---|
| OR15 | 38.2554 | 15.5757 | 18.1881 | 1.1678 | 2.1033 |
| OR16 | 37.9466 | 15.4301 | 18.5091 | 1.1996 | 2.0502 |

Data shown in tables 5 and 6 are source data representing Pb isotopes contained in AD, NAD, NAD, and desert soil, and acquired from various samples obtained in 2007 and 2008 as described above.

In addition, the average values of Pb isotopes contained in AD, NAD, NAD, and desert soil are shown in table 7.

TABLE 7

| Nationals | Regions | | | $^{208}Pb/^{204}Pb$ | $^{207}Pb/^{204}Pb$ | $^{206}Pb/^{204}Pb$ | $^{206}Pb/^{207}Pb$ | $^{208}Pb/^{206}Pb$ |
|---|---|---|---|---|---|---|---|---|
| Korea | Daejeon; this study | Asian dust | Mean | 38.1336 ± 0.0828 | 15.6032 ± 0.0164 | 18.2290 ± 0.1064 | 1.1683 ± 0.0059 | 2.0919 ± 0.0105 |
| | | | Range | 37.9896-38.2485 | 15.5828-15.6269 | 18.0778-18.3782 | 1.1596-1.1761 | 2.0792-2.1047 |
| | | non-Asian dust | Mean | 38.0418 ± 0.1062 | 15.5902 ± 0.0151 | 18.0782 ± 0.1043 | 1.1596 ± 0.0059 | 2.1048 ± 0.0086 |
| | | | Range | 37.8316-38.2586 | 15.5667-15.621 | 17.8459-18.2083 | 1.146-1.1667 | 2.0931-2.1248 |
| | | Dry deposition of Asian dust | Mean | 37.9999 ± 0.1892 | 15.5916 ± 0.0237 | 17.9423 ± 0.1529 | 1.1508 ± 0.0097 | 2.1179 ± 0.0107 |
| | | | Range | 37.7013-38.2254 | 15.5553-15.6150 | 17.7676-18.1940 | 1.1421-1.1673 | 2.1008-2.1317 |
| | | Dry deposition of non-Asian dust | Mean | 38.0700 ± 0.1866 | 15.5964 ± 0.0286 | 17.9842 ± 0.0832 | 1.1531 ± 0.0047 | 2.1169 ± 0.0062 |
| | | | Range | 37.7185-38.3149 | 15.5580-15.6386 | 17.8190-18.0503 | 1.1449-1.1578 | 2.1090-2.1252 |
| | | Regional soil | Mean | 38.7959 ± 0.4485 | 15.5975 ± 0.0935 | 18.4400 ± 0.1507 | 1.1822 ± 0.0060 | 2.1038 ± 0.0096 |
| | | | Range | 38.2409-39.2862 | 15.4805-15.6787 | 18.2171-18.5800 | 1.1753-1.1896 | 2.0915-2.1145 |
| China | Desert soil; this study | Loess | Mean | 38.7588 ± 0.3142 | 15.6020 ± 0.0829 | 18.7295 ± 0.0818 | 1.2005 ± 0.0026 | 2.0693 ± 0.0083 |
| | | | Range | 38.1834-39.0912 | 15.4261-15.6567 | 18.5814-18.8507 | 1.1968-1.2056 | 2.0531-2.0761 |
| | | Taklamakan | Mean | 38.5649 ± 0.3233 | 15.5671 ± 0.0975 | 18.5975 ± 0.0741 | 1.1947 ± 0.0036 | 2.0736 ± 0.0100 |
| | | | Range | 37.8933-38.9205 | 15.3710-15.6538 | 18.4292-18.6681 | 1.1909-1.2025 | 2.0560-2.0848 |
| | | Alashan | Mean | 38.4868 ± 0.1683 | 15.5877 ± 0.0323 | 18.3597 ± 0.1870 | 1.1778 ± 0.0105 | 2.0964 ± 0.0127 |
| | | | Range | 38.2134-38.6463 | 15.5514-15.6268 | 18.0671-18.5192 | 1.1671-1.1853 | 2.0868-2.1151 |
| | | Ordos | Mean | 37.5987 ± 0.1907 | 15.3976 ± 0.0529 | 17.3046 ± 0.1611 | 1.1239 ± 0.0081 | 2.1675 ± 0.0130 |
| | | | Range | 37.2497-37.8822 | 15.2709-15.4434 | 16.9844-17.497 | 1.1106-1.1332 | 2.1518-2.1941 |
| | | | Mean | 38.4680 ± 0.3657 | 15.5625 ± 0.0786 | 18.5288 ± 0.2056 | 1.1907 ± 0.0130 | 2.0762 ± 0.0188 |
| | | | Range | 37.9466-38.8330 | 15.4301-15.6240 | 18.1881-18.6924 | 1.1678-1.1996 | 2.0502-2.1033 |
| | | | | | Literature data | | | |
| Korea | Seoul | Roadside Sediment [a] | Mean | 38.3278 ± 0.2884 | 15.6343 ± 0.0337 | 18.0992 ± 0.1356 | 1.1576 ± 0.0068 | 2.1177 ± 0.0151 |
| | | | Range | 37.8202-39.0121 | 15.5688-15.6766 | 17.7782-18.2564 | 1.1419-1.1681 | 2.0987-2.1536 |
| | | Airborne Particles (1987-1988) [b] | Mean | | | | 1.1620 ± 0.0104 | 2.1153 ± 0.0248 |
| | | | Range | | | | 1.14-1.18 | |
| | | Airborne Particles (1994-1995) [c] | Mean | | | 17.97 ± 0.02 | 1.150 ± 0.001 | |
| | | | Range | | | | | |
| China | Beijing | Airborne Particles (1988, winter) [b] | Mean | | | | 1.1376 ± 0.0022 | 2.1239 ± 0.0060 |
| | | Airborne Particles (1996-1997) [d] | | | | 17.78 ± 0.14 | 1.1484 ± 0.002 | 2.129 ± 0.007 |
| | Changchun Dalian | Airborne Particles (1996-1997) [d] | | | | 18.09 ± 0.13 | 1.1655 ± 0.005 | 2.113 ± 0.009 |
| | | Airborne Particles (1996-1997) [d] | | | | 17.69 ± 0.12 | 1.1351 ± 0.003 | 2.151 ± 0.006 |
| | Shanghai Nanjing | Airborne Particles (1996-1997) [d] | | | | 18.06 ± 0.09 | 1.1561 ± 0.003 | 2.118 ± 0.002 |
| | | Airborne Particles (1996-1997) [d] | | | | 18.20 ± 0.08 | 1.1614 ± 0.001 | 2.118 ± 0.004 |
| | Harbin Guanzhou | Airborne Particles (1996-1997) [d] | | | | 18.22 ± 0.14 | 1.1723 ± 0.004 | 2.098 ± 0.006 |
| | | Eolian dusts (1992) [e] | | 38.5162 ± 0.1919 | 15.6696 ± 0.0379 | 18.29 ± 0.10 | 1.1675 ± 0.0052 | |
| | Foshan | Eolian dusts (1992) [e] | | 38.8163 ± 0.1426 | 15.7473 ± 0.0514 | 18.33 ± 0.04 | 1.1636 ± 0.0026 | |

In table 7, some literature data are added for reference, and obtained from [a]Lee et al. (2005), [b]Mukai et al. (1993); [c]Bollhoefer and Rosman (2001), [d]Mukai et al. (2001), and [e]Zhu et al. (2001).

Meanwhile, Pb isotope values from various coal and lead mines in China are shown in table 8.

Table 8 contains AD and NAD-related data obtained from in Dae Jeon, South Korea, and other Pb isotopes obtained from various coal and lead mines in China may be obtained from [a]Lee et al. (2013), [b]Lee et al. (2005), [c]Mukai et al. (1993), [d]Bollhoefer and Rosman (2001), [e]Mukai et al.

TABLE 8

| Nationals | Regions | | | $^{208}Pb/^{204}Pb$ | $^{207}Pb/^{204}Pb$ | $^{206}Pb/^{204}Pb$ | $^{206}Pb/^{207}Pb$ | $^{208}Pb/^{206}Pb$ |
|---|---|---|---|---|---|---|---|---|
| Korea | Daejeon; this study | Asian dust (N = 4) | Mean ± S.D | 38.1203 ± 0.0908 | 15.5975 ± 0.0146 | 18.2375 ± 0.1167 | 1.1693 ± 0.0067 | 2.0903 ± 0.0102 |
| | | | Range | 37.9896-38.1952 | 15.5868-15.6189 | 18.1367-18.3682 | 1.1631-1.1760 | 2.0794-2.1025 |
| | | non-Asian dust (N = 3) | Mean ± S.D | 38.0203 ± 0.1634 | 15.5886 ± 0.0201 | 18.1059 ± 0.0953 | 1.1615 ± 0.0047 | 2.0998 ± 0.0068 |
| | | | Range | 37.8316-38.1163 | 15.5667-15.6063 | 18.0199-18.2083 | 1.1576-1.1667 | 2.0933-2.1068 |
| | | Regional soil (N = 5) | Mean ± S.D | 38.7959 ± 0.4485 | 15.5975 ± 0.0935 | 18.4400 ± 0.1507 | 1.1822 ± 0.0060 | 2.1038 ± 0.0096 |
| | | | Range | 38.2409-39.2862 | 15.4805-15.6787 | 18.2171-18.5800 | 1.1753-1.1896 | 2.0915-2.1145 |
| | | | | Literature data | | | | |
| Korea | Seoul | Roadside Sediment [b] | Mean ± S.D | 38.3278 ± 0.2884 | 15.6343 ± 0.0337 | 18.0992 ± 0.1356 | 1.1576 ± 0.0068 | 2.1177 ± 0.0151 |
| | | | Range | 37.8202-39.0121 | 15.5688-15.6766 | 17.7782-18.2564 | 1.1419-1.1681 | 2.0987-2.1536 |
| | | Airborne Particles (1987-1988) [c] | Mean ± S.D | | | | 1.1620 ± 0.0104 | 2.1153 ± 0.0248 |
| | | | Range | | | | 1.14-1.18 | |
| | | Airborne particles (1994-1995) [d] | Mean ± S.D | | | 17.97 ± 0.02 | 1.150 ± 0.001 | |
| China | Beijing | Airborne Particles (1988, winter) [c] | Mean ± S.D | | | | 1.1376 ± 0.0022 | 2.1239 ± 0.0060 |
| | | Airborne Particles (1996-1997) [e] | Mean ± S.D | | | 17.78 ± 0.14 | 1.1484 ± 0.002 | 2.129 ± 0.007 |
| | Changchun | Airborne Particles (1996-1997) [e] | Mean ± S.D | | | 18.09 ± 0.13 | 1.1655 ± 0.005 | 2.113 ± 0.009 |
| | Dalian | Airborne Particles (1996-1997) [e] | Mean ± S.D | | | 17.69 ± 0.12 | 1.1351 ± 0.003 | 2.151 ± 0.006 |
| | Shanghai | Airborne Particles [f] | Mean ± S.D | | | 18.14 ± 0.08 | 1.1617 ± 0.002 | 2.105 ± 0.005 |
| | Nanjing | Airborne Particles (1996-1997) [e] | Mean ± S.D | | | 18.20 ± 0.08 | 1.1614 ± 0.001 | 2.118 ± 0.004 |
| | Harbin | Airborne Particles (1996-1997) [e] | Mean ± S.D | | | 18.22 ± 0.14 | 1.1723 ± 0.004 | 2.098 ± 0.006 |
| | Guanzhou | Eolian dusts (1992) [g] | Mean ± S.D | 38.5162 ± 0.1919 | 15.6696 ± 0.0379 | 18.29 ± 0.10 | 1.1675 ± 0.0052 | |
| | Foshan | Eolian dusts (1992) [g] | Mean ± S.D | 38.8163 ± 0.1426 | 15.7473 ± 0.0514 | 18.33 ± 0.04 | 1.1636 ± 0.0026 | |
| | Shanghai | Coal [h] | Mean ± S.D | | | | 1.1627 ± 0.010 | |
| | | Coal combustion dust [h] | Mean ± S.D | | | | 1.1668 ± 0.002 | |
| | | Coal fly ash [h] | Mean ± S.D | | | | 1.1655 ± 0.002 | |
| | Northern China coal Pb ore deposit | Coal [c] | Mean ± S.D | | | | 1.1781 ± 0.0218 | 2.1007 ± 0.0298 |
| | | Binggou [i] | Mean ± S.D | | | | 1.0660 ± 0.0039 | 2.2493 ± 0.0065 |
| | | Dongshan [i] | Mean ± S.D | | | | 1.0676 ± 0.0072 | 2.2508 ± 0.0143 |
| | | Fankou [i] | Mean ± S.D | | | | 1.1720 ± 0.0016 | 2.1096 ± 0.0024 |
| | | Guanmenshan [i] | Mean ± S.D | | | | 1.0259 ± 0.0469 | 2.2626 ± 0.1020 |
| | | Gudonggou [i] | Mean ± S.D | | | | 1.0681 ± 0.0055 | 2.2473 ± 0.0102 |
| | | Jiashenpan [i] | Mean ± S.D | | | | 1.0415 ± 0.0063 | 2.2424 ± 0.0204 |
| | | Jinding [i] | Mean ± S.D | | | | 1.1789 ± 0.0004 | 2.0957 ± 0.0009 |
| | | Lugou [i] | Mean ± S.D | | | | 1.0661 ± 0.0024 | 2.2492 ± 0.0080 |

(2001), [f]Zheng et al. (2004), [g]Zhu et al. (2001), [h]Chen et al. (2005), and [i]Sangster et al. (2000).

As described above, the analysis results of Pb stable isotopes after Pb stable isotopes has been eluted from previously prepared samples through the sequential extraction scheme including phase 1 (S110) to phase 5 (S150) as described above are summarized in tables 9 to 11 which include original data.

Table 9 shows the values of Pb isotopes contained in NAD, that is, source data, table 10 shows the values of Pb isotopes measured after elution through the sequential extraction scheme, and table 11 shows the average values of the Pb isotopes measured after melting through the sequential extraction scheme.

TABLE 9

| Regions | Sample name | $^{206}Pb/^{204}Pb$ | $^{207}Pb/^{204}Pb$ | $^{208}Pb/^{204}Pb$ | $^{206}Pb/^{207}Pb$ | $^{208}Pb/^{206}Pb$ |
|---|---|---|---|---|---|---|
| non-Asia dust | blank filter-1 | 21.718 | 15.846 | 38.618 | 1.3705 | 1.7780 |
| | blank filter-2 | 21.802 | 15.806 | 38.423 | 1.3794 | 1.7623 |
| | F61-PM2.5 | 18.558 | 15.643 | 37.955 | 1.1864 | 2.0448 |
| | F73-PM2.5 | 18.320 | 15.611 | 38.213 | 1.1736 | 2.0857 |
| | F95-PM2.5 | 18.267 | 15.615 | 38.176 | 1.1698 | 2.0901 |
| | F106-PM2.5 | 18.328 | 15.605 | 38.091 | 1.1746 | 2.0782 |
| | F119-PM2.5 | 18.417 | 15.692 | 38.428 | 1.1736 | 2.0866 |
| | F126-PM2.5 | 18.624 | 15.644 | 37.988 | 1.1905 | 2.0397 |
| | F133-PM2.5 | 18.621 | 15.624 | 37.919 | 1.1918 | 2.0363 |
| | F136-PM2.5 | 18.624 | 15.665 | 38.369 | 1.1888 | 2.0601 |
| | F139-PM2.5 | 18.823 | 15.646 | 38.166 | 1.2031 | 2.0277 |
| | F142-PM2.5 | 18.415 | 15.631 | 37.779 | 1.1781 | 2.0514 |
| | F145-PM2.5 | 18.326 | 15.676 | 38.236 | 1.1690 | 2.0865 |
| | F146-PM2.5 | 17.894 | 15.611 | 37.851 | 1.1462 | 2.1153 |
| | F151-PM2.5 | 18.311 | 15.654 | 38.333 | 1.1697 | 2.0934 |
| | F157-PM2.5 | 18.262 | 15.630 | 38.110 | 1.1684 | 2.0869 |
| | F160-PM2.5 | 18.335 | 15.628 | 38.171 | 1.1733 | 2.0817 |
| | | | | | 1.1763 | |

TABLE 10

| Sample name | fraction | $^{206}Pb/^{204}Pb$ | $^{207}Pb/^{204}Pb$ | $^{208}Pb/^{204}Pb$ | $^{206}Pb/^{207}Pb$ | $^{208}Pb/^{206}Pb$ |
|---|---|---|---|---|---|---|
| non-Asian dust 23 | I-IV | 38.2357 | 15.6321 | 18.0538 | 1.1548 | 2.1179 |
| | V | 39.0675 | 15.8364 | 18.4744 | 1.1665 | 2.1142 |
| non-Asian dust 25 | I-IV | 38.0637 | 15.6168 | 17.9685 | 1.1508 | 2.1176 |
| | V | 38.8148 | 15.7595 | 18.3559 | 1.1648 | 2.1145 |
| Asian dust 5 | I-IV | 37.8291 | 15.6026 | 17.8202 | 1.1422 | 2.1228 |
| | V | 38.7280 | 15.7268 | 18.4347 | 1.1722 | 2.1004 |
| Asian-dust 6 | I-IV | 38.0312 | 15.6294 | 17.9736 | 1.1508 | 2.1157 |
| | V | 38.8642 | 15.7766 | 18.4987 | 1.1726 | 2.1013 |
| Asian-dust 7 | I-IV | 38.2514 | 15.6100 | 18.1878 | 1.1652 | 2.1033 |
| | V | 38.9217 | 15.7865 | 18.5974 | 1.1781 | 2.0929 |
| Asian-dust 8 | I-IV | 38.0203 | 15.6016 | 17.9904 | 1.1531 | 2.1134 |
| | V | 38.8924 | 15.8115 | 18.5234 | 1.1714 | 2.0996 |
| Asian-dust 9 | I-IV | 38.2550 | 15.6622 | 18.1840 | 1.1610 | 2.1040 |
| | V | 38.7972 | 15.7020 | 18.5050 | 1.1785 | 2.0967 |
| Alashan | I-IV | 38.8198 | 15.6780 | 18.8116 | 1.1998 | 2.0636 |
| | V | 38.5264 | 15.6232 | 18.4199 | 1.1786 | 2.0922 |
| Taklamakan | I-IV | 38.7647 | 15.6792 | 18.6869 | 1.1918 | 2.0746 |
| | V | 38.8971 | 15.6928 | 18.6692 | 1.1898 | 2.0832 |
| Loess | I-IV | 38.8381 | 15.6661 | 18.7143 | 1.1945 | 2.0754 |
| | V | 39.3365 | 15.7608 | 18.9501 | 1.2025 | 2.0756 |
| Ordos | I-IV | 38.8110 | 15.6595 | 18.6985 | 1.1940 | 2.0757 |
| | V | 39.1685 | 15.7211 | 18.7788 | 1.1945 | 2.0857 |

TABLE 11

| Sample name | fraction | $^{206}Pb/^{204}Pb$ | $^{207}Pb/^{204}Pb$ | $^{208}Pb/^{204}Pb$ | $^{206}Pb/^{207}Pb$ | $^{208}Pb/^{206}Pb$ |
|---|---|---|---|---|---|---|
| non-Asian dust | I-IV | 38.1497 | 15.6244 | 18.0114 | 1.1528 | 2.1178 |
| | V | 38.9412 | 15.7980 | 18.4151 | 1.1656 | 2.1144 |
| Asian-dust | I-IV | 38.0774 | 15.6212 | 18.0312 | 1.1543 | 2.1118 |
| | V | 38.8407 | 15.7607 | 18.5118 | 1.1746 | 2.0982 |
| Alashan | I-IV | 38.8198 | 15.6780 | 18.8116 | 1.1998 | 2.0636 |
| | V | 38.5264 | 15.6232 | 18.4199 | 1.1786 | 2.0922 |
| Taklamakan | I-IV | 38.7647 | 15.6792 | 18.6869 | 1.1918 | 2.0746 |
| | V | 38.8971 | 15.6928 | 18.6692 | 1.1898 | 2.0832 |
| Loess | I-IV | 38.8381 | 15.6661 | 18.7143 | 1.1945 | 2.0754 |
| | V | 39.3365 | 15.7608 | 18.9501 | 1.2025 | 2.0756 |
| Ordos | I-IV | 38.8110 | 15.6595 | 18.6985 | 1.1940 | 2.0757 |
| | V | 39.1685 | 15.7211 | 18.7788 | 1.1945 | 2.0857 |

In particular, as recognized from tables 9 and 11, the values of $^{206}Pb/^{207}Pb$, which are preferable data according to the present invention, are marked in bold.

Finally, the average values of Pb concentration and Pb isotopes in various samples, and the average value obtained through the sequential extraction result are summarized as shown in table 12.

Hereinafter, the method of resolving the contribution ratio to the soil contamination by a plurality of polluters through the sequential extraction scheme and the stable isotope analysis scheme will be described with reference to table 12 if it is not a special case.

TABLE 12

| Sample | | Pb concentration | Average value of Pb isotope | Average value Of sequential extraction results |
|---|---|---|---|---|
| AD | TSP | 850 | 1.1683 | |
| | PM10 | 957 | | |
| | PM2.5 | 2890 | | |
| NAD | TSP | 783 | 1.1596(1.1763) | |
| | PM10 | 935 | | |
| | PM2.5 | 2520 | | |
| AD precipitate | | 140.1 | 1.1508 | 1.1542/1.1745 |
| NAD precipitate | | 367.9 | 1.1531 | 1.1528/1.1656 |
| Desert Soil (the Alashan desert) | | 14.7 | 1.1778 | 1.1998/1.1786 |
| Chinese atmospheric dust | | 159.7 | 1.1653/1.1580 | |
| Chinese coal | | | 1.1683 | |
| Chinese lead mines | | | 1.0559/1.0857 | |

As described above, the method of resolving the contribution ratio to the soil contamination by a plurality of polluters through the sequential extraction scheme and the stable isotope analysis scheme will be described with reference to table 12 for the illustrative purpose.

1) Regarding AD
1-1. TSP

The values of Pb isotopes derived from the anthropogenic pollution may be calculated as follows.

$$(^{206}Pb/^{207}Pb)_{anthr}=(850\times1.1683-14.7\times1.1778)/(850-14.7)=1.1681$$

The ratio of anthropogenic pollution to geogenic pollution is calculated as follows by using the values of the Pb isotopes derived from the anthropogenic pollution.

$$(Pb\ \%)_{anthr}=(1.1778-1.1683)/(1.1778-1.1681)\times100=97.9\%$$

In other words, the anthropogenic pollution is 97.9%.
In this case, the relative anthropogenic pollution ratio may be calculated as follows by distinguishing between the coal combustion and the industrial activity using Pb.

$$(Pb)_{coal}=(1.0857-1.1681)/(1.0857-1.1683)\times100=99.7\%$$

In other words, regarding an anthropogenic pollution source, the Pb pollution from coal has the contribution ratio of 99.7%, and the Pb pollution from the industrial activity has the contribution ratio of 0.3%.

1-2. PM10
The value of the Pb isotope derived from the anthropogenic pollution may be calculated as follows.

$$(^{206}Pb/^{207}Pb)_{anthr}=(957\times1.1683-14.7\times1.1778)/(957-14.7)=1.1681$$

The ratio of the anthropogenic pollution to the geogenic pollution is calculated as follows using the value of the Pb isotope derived from the anthropogenic pollution.

$$(Pb\ \%)_{anthr}=(1.1778-1.1683)/(1.1778-1.1681)\times100=97.9\%$$

In other words, the anthropogenic pollution is 97.9%.
In this case, the relative anthropogenic pollution ratio may be calculated as follows by distinguishing between the coal combustion and the industrial activity using Pb.

$$(Pb)_{coal}=(1.0857-1.1681)/(1.0857-1.1683)\times100=99.7\%$$

In other words, regarding an anthropogenic pollution source, the Pb pollution from coal has the contribution ratio of 99.7%, and the Pb pollution from the industrial activity has the contribution ratio of 0.3%.

1-3. PM2.5
The value of the Pb isotope derived from the anthropogenic pollution may be calculated as follows.

$$(^{206}Pb/^{207}Pb)_{anthr}=(2890\times1.1683-14.7\times1.1778)/(2890-14.7)=1.1682$$

The ratio of the anthropogenic pollution to the geogenic pollution is calculated as follows using the value of the Pb isotope derived from the anthropogenic pollution.

$$(Pb\ \%)_{anthr}=(1.1778-1.1683)/(1.1778-1.1682)\times100=98.9\%$$

In other words, the anthropogenic pollution is 98.9%.
In this case, the relative anthropogenic pollution ratio may be calculated as follows by distinguishing between the coal combustion and the industrial activity using Pb.

$$(Pb)_{coal}=(1.0857-1.1681)/(1.0857-1.1683)\times100=99.8\%$$

In other words, regarding an anthropogenic pollution source, the Pb pollution from coal has the contribution ratio of 99.8%, and the Pb pollution from the industrial activity has the contribution ratio of 0.2%.

2) NAD
2-1. TSP
The value of the Pb isotope derived from the anthropogenic pollution may be calculated as follows.

$$(^{206}Pb/^{207}Pb)_{anthr}=(783\times1.1596-14.7\times1.1778)/(783-14.7)=1.1592$$

The ratio of the anthropogenic pollution to the geogenic pollution is calculated as follows using the value of the Pb isotope derived from the anthropogenic pollution.

$$(Pb\ \%)_{anthr}=(1.1778-1.1596)/(1.1778-1.1592)\times100=97.8\%$$

In other words, the anthropogenic pollution is 97.8%.
In this case, the relative anthropogenic pollution ratio may be calculated as follows by distinguishing between the coal combustion and the industrial activity using Pb.

$$(Pb)_{coal}=(1.0857-1.1592)/(1.0857-1.1596)\times100=99.4\%$$

In other words, regarding an anthropogenic pollution source, the Pb pollution from coal has the contribution ratio of 99.4%, and the Pb pollution from the industrial activity has the contribution ratio of 0.6%.

2-2. PM10
The value of the Pb isotope derived from the anthropogenic pollution may be calculated as follows.

$$(^{206}Pb/^{207}Pb)_{anthr}=(935\times1.1596-14.7\times1.1778)/(935-14.7)=1.1593$$

The ratio of the anthropogenic pollution to the geogenic pollution is calculated as follows using the value of the Pb isotope derived from the anthropogenic pollution.

$$(Pb\ \%)_{anthr}=(1.1778-1.1596)/(1.1778-1.1593)\times100=98.3\%$$

In other words, the anthropogenic pollution is 98.3%.

In this case, the relative anthropogenic pollution ratio may be calculated as follows by distinguishing between the coal combustion and the industrial activity using Pb.

$$(Pb)_{coal}=(1.0857-1.1593)/(1.0857-1.1596)\times100=99.5\%$$

In other words, regarding an anthropogenic pollution source, the Pb pollution from coal has the contribution ratio of 99.5%, and the Pb pollution from the industrial activity has the contribution ratio of 0.5%.

2-3. PM2.5

The value of the Pb isotope derived from the anthropogenic pollution may be calculated as follows.

$$(^{206}Pb/^{207}Pb)_{anthr}=(2520\times1.1596-14.7\times1.1778)/(2520-14.7)=1.1594$$

The ratio of the anthropogenic pollution to the geogenic pollution is calculated as follows using the value of the Pb isotope derived from the anthropogenic pollution.

$$(Pb\ \%)_{anthr}=(1.1778-1.1596)/(1.1778-1.1594)\times100=98.9\%$$

In other words, the anthropogenic pollution is 98.9%.

In this case, the relative anthropogenic pollution ratio may be calculated as follows by distinguishing between the coal combustion and the industrial activity using Pb.

$$(Pb)_{coal}=(1.0857-1.1594)/(1.0857-1.1596)\times100=99.7\%$$

In other words, regarding an anthropogenic pollution source, the Pb pollution from coal has the contribution ratio of 99.7%, and the Pb pollution from the industrial activity has the contribution ratio of 0.3%.

3) NAD

As described below, in the case of NAD, TSP, PM10, and PM 2.5 are completely matched with each other.

3-1. TSP

The value of the Pb isotope derived from the anthropogenic pollution may be calculated as follows.

$$(^{206}Pb/^{207}Pb)_{anthr}=(783\times1.1763-14.7\times1.1778)/(783-14.7)=1.1762$$

The ratio of the anthropogenic pollution to the geogenic pollution is calculated as follows using the value of the Pb isotope derived from the anthropogenic pollution.

$$(Pb\ \%)_{anthr}=(1.1778-1.1763)/(1.1778-1.1762)\times100=93.7\%$$

In other words, the anthropogenic pollution is 93.7%.

In this case, the relative anthropogenic pollution ratio may be calculated as follows by distinguishing between the coal combustion and the industrial activity using Pb.

$$(Pb)_{coal}=(1.0857-1.1762)/(1.0857-1.1763)\times100=99.8\%$$

In other words, regarding an anthropogenic pollution source, the Pb pollution from coal has the contribution ratio of 99.8%, and the Pb pollution from the industrial activity has the contribution ratio of 0.2%.

3-2. PM10

The value of the Pb isotope derived from the anthropogenic pollution may be calculated as follows.

$$(^{206}Pb/^{207}Pb)_{anthr}=(935\times1.1763-14.7\times1.1778)/(935-14.7)=1.1762$$

The ratio of the anthropogenic pollution to the geogenic pollution is calculated as follows using the value of the Pb isotope derived from the anthropogenic pollution.

$$(Pb\ \%)_{anthr}=(1.1778-1.1763)/(1.1778-1.1762)\times100=93.7\%$$

In other words, the anthropogenic pollution is 93.7%.

In this case, the relative anthropogenic pollution ratio may be calculated as follows by distinguishing between the coal combustion and the industrial activity using Pb.

$$(Pb)_{coal}=(1.0857-1.1762)/(1.0857-1.1763)\times100=99.8\%$$

In other words, regarding an anthropogenic pollution source, the Pb pollution from coal has the contribution ratio of 99.8%, and the Pb pollution from the industrial activity has the contribution ratio of 0.2%.

3-3. PM2.5

The value of the Pb isotope derived from the anthropogenic pollution may be calculated as follows.

$$(^{206}Pb/^{207}Pb)_{anthr}=(2520\times1.1763-14.7\times1.1778)/(2520-14.7)=1.1762$$

The ratio of the anthropogenic pollution to the geogenic pollution is calculated as follows using the value of the Pb isotope derived from the anthropogenic pollution.

$$(Pb\ \%)_{anthr}=(1.1778-1.1763)/(1.1778-1.1762)\times100=93.7\%$$

In other words, the anthropogenic pollution is 93.7%.

In this case, the relative anthropogenic pollution ratio may be calculated as follows by distinguishing between the coal combustion and the industrial activity using Pb.

$$(Pb)_{coal}=(1.0857-1.1762)/(1.0857-1.1763)\times100=99.8\%.$$

In other words, regarding an anthropogenic pollution source, the Pb pollution from coal has the contribution ratio of 99.8%, and the Pb pollution from the industrial activity has the contribution ratio of 0.2%.

4) AD Sediment

The value of the Pb isotope derived from the anthropogenic pollution may be calculated as follows.

$$(^{206}Pb/^{207}Pb)_{anthr}=(140.1\times1.1508-14.7\times1.1778)/(140.1-14.7)=1.1476$$

The ratio of the anthropogenic pollution to the geogenic pollution is calculated as follows using the value of the Pb isotope derived from the anthropogenic pollution.

$$(Pb\ \%)_{anthr}=(1.1778-1.1508)/(1.1778-1.1476)\times100=89.4\%$$

In other words, the anthropogenic pollution is 89.4%.

In this case, the relative anthropogenic pollution ratio may be calculated as follows by distinguishing between the coal combustion and the industrial activity using Pb.

$$(Pb)_{coal}=(1.0857-1.1476)/(1.0857-1.1683)\times100=74.9\%$$

In other words, regarding an anthropogenic pollution source, the Pb pollution from coal has the contribution ratio of 74.9%, and the Pb pollution from the industrial activity has the contribution ratio of 25.1%.

5) NAD Sediment

The value of the Pb isotope derived from the anthropogenic pollution may be calculated as follows.

$(^{206}Pb/^{207}Pb)_{anthr}=(367.9\times1.1531-14.7\times1.1778)/(367.9-14.7)=1.1520$ The ratio of the anthropogenic pollution to the geogenic pollution is calculated as follows using the value of the Pb isotope derived from the anthropogenic pollution.

$(Pb\%)_{anthr}=(1.1778-1.1531)/(1.1778-1.1520)\times100=95.7\%$

In other words, the anthropogenic pollution is 95.7%.

In this case, the relative anthropogenic pollution ratio may be calculated as follows by distinguishing between the coal combustion and the industrial activity using Pb.

$(Pb)_{coal}=(1.0857-1.1520)/(1.0857-1.1683)\times100=80.2\%$

In other words, regarding an anthropogenic pollution source, the Pb pollution from coal has the contribution ratio of 80.2%, and the Pb pollution from the industrial activity has the contribution ratio of 19.8%.

6) AD Sediment: Sequential Extraction Scheme

The value of the Pb isotope derived from the anthropogenic pollution may be calculated as follows.

$(^{206}Pb/^{207}Pb)_{anthr}=(140.1\times1.1542-14.7\times1.1745)/(140.1-14.7)=1.1518$ The ratio of the anthropogenic pollution to the geogenic pollution is calculated as follows using the value of the Pb isotope derived from the anthropogenic pollution.

$(Pb\%)_{anthr}=(1.1745-1.1542)/(1.1745-1.1518)\times100=89.4\%$

In other words, the anthropogenic pollution is 89.4%.

In this case, the relative anthropogenic pollution ratio may be calculated as follows by distinguishing between the coal combustion and the industrial activity using Pb.

$(Pb)_{coal}=(1.0857-1.1518)/(1.0857-1.1683)\times100=80.0\%$

In other words, regarding an anthropogenic pollution source, the Pb pollution from coal has the contribution ratio of 80.0%, and the Pb pollution from the industrial activity has the contribution ratio of 20.0%.

7) NAD Sediment: Sequential Extraction Scheme

The value of the Pb isotope derived from the anthropogenic pollution may be calculated as follows.

$(^{206}Pb/^{207}Pb)_{anthr}=(367.9\times1.1528-14.7\times1.1656)/(367.9-14.7)=1.1522$ The ratio of the anthropogenic pollution to the geogenic pollution is calculated as follows using the value of the Pb isotope derived from the anthropogenic pollution.

$(Pb\%)_{anthr}=(1.1656-1.1528)/(1.1656-1.1522)\times100=95.5\%$

In other words, the anthropogenic pollution is 95.5%.

In this case, the relative anthropogenic pollution ratio may be calculated as follows by distinguishing between the coal combustion and the industrial activity using Pb.

$(Pb)_{coal}=(1.0857-1.1522)/(1.0857-1.1683)\times100=80.5\%$

In other words, regarding an anthropogenic pollution source, the Pb pollution from coal has the contribution ratio of 80.5%, and the Pb pollution from the industrial activity has the contribution ratio of 19.5%.

Although the method of the resolving contribution ratio to soil contamination by plurality of polluters through the sequential extraction scheme and the stable isotope analysis scheme according to an exemplary embodiment of the present invention has been described for the illustrative purpose, it should be understood that the present invention should not be limited thereto. In other words, the present invention is applicable to soil existing in a workplace, such as an abandoned mine, a smelter, or a steel mill, that discharges pollution materials including a large amount of heavy metal, and seabed soil as described above.

For example, according to an exemplary embodiment of the present invention, when recovering a natural environment, or estimating natural environmental damages, the contribution ratio to pollution by an agent responsible for the pollution can be resolved, so that environmental charges to be imposed on the agent can be resolved and specified.

Although exemplary embodiments of the present invention has been described for the illustrative purpose, it should be understood that the present invention is not limited to these exemplary embodiments but various changes, modifications, equivalents can be made by one ordinary skilled in the art within the spirit and scope of the present invention as hereinafter claimed.

What is claimed is:

1. A method of resolving a contribution ratio to soil contamination by a plurality of polluters through a sequential extraction scheme and a stable isotope analysis scheme, the method comprising:

performing the sequential extraction scheme (S100); and applying an equation of resolving the contribution ratio to the soil contamination to an analysis value of a stable isotope obtained through the sequential extraction scheme (S100), wherein the performing of the sequential extraction scheme (S100) comprises:

(A) preparing a first sample containing a Pb stable isotope;

(B) preparing a first solution of 1M $MgCl_2$, pH=7, introducing the first sample into the first solution, and stirring the first sample at a normal temperature for one hour to obtain a second solution, and recovering a second sample which is the first sample remaining without being dissolved;

(C) preparing a third solution of 1M $CH_3COONa$, adjusting acidity (pH) of the third solution to 5 using HOAc, introducing the second sample into the third solution, and stirring the second sample at a normal temperature for five hours to obtain a fourth solution, and recovering a third sample which is the second sample remaining without being dissolved;

(D) preparing a fifth solution of 0.04M $NH_2OH\cdot HCl$ and 25% HOAc, adjusting acidity (pH) of the fifth solution to 2, introducing the third sample into the fifth solution, and heating the third sample at a temperature of 96° C. for six hours to obtain a sixth solution, and recovering a fourth sample which is the third sample remaining without being dissolved;

(E) preparing a seventh solution of 30% $H_2O_2$ and 0.02M $HNO_3$, introducing the fourth sample into the seventh solution, cooling the fourth sample at a temperature of 85° C. for five hours, additionally introducing an eighth solution of 3.2M $NH_4OAc$ and 20% $HNO_3$ into the seventh solution, and performing stirring at a normal temperature for 30 minutes to obtain a ninth solution, and recovering a fifth sample which is the fourth sample remaining without being dissolved;

(F) introducing the fifth sample into a tenth solution of HF and HClO$_4$, completely drying the fifth sample through evaporation at a temperature of 110° C., introducing a 12M HCl solution, and performing heating for 30 minutes to completely dissolve the fifth sample and to obtain an eleventh solution; and (G) analyzing contents of Pb stable isotopes contained in Pb stable isotope eluates of the second, fourth, sixth, ninth, and eleventh solutions obtained in steps (B) to (F), wherein the Pb stable isotopes used in step (G) of analyzing the contents of the Pb stable isotopes are $^{206}$Pb and $^{207}$Pb, wherein $^{206}$Pb/$^{207}$Pb values measured from the second, fourth, sixth, and ninth solutions are anthropogenic Pb stable isotope values resulting from a human activity, wherein a $^{206}$Pb/$^{207}$Pb value measured from the eleventh solution is a geogenic Pb stable isotope value resulting from a natural activity, wherein in the applying of the equation of resolving the contribution ratio (S200), the anthropogenic Pb stable isotope values are obtained through Equation I, $$(^{206}Pb/^{207}Pb)_{Anthr.} = \frac{[C_{meas} \times (^{206}Pb/^{207}Pb)_{meas}] - [C_{back} \times (^{206}Pb/^{207}Pb)_{back}]}{C_{meas} - C_{back}} \quad \text{Equation I}$$

in which $(^{206}Pb/^{207}Pb)_{anthr.}$ denotes a Pb stable isotope value by anthropogenic pollution, $(^{206}Pb/^{207}Pb)_{meas}$ denotes a Pb stable isotope value of an analyte, $(^{206}Pb/^{207}Pb)_{back}$ denotes a geogenic (natural) Pb stable isotope value, $C_{meas}$ denotes a content of Pb contained in the analyte to be measured, and $C_{back}$ denotes a content of geogenic (natural) Pb, and wherein the contribution ratio is resolved and specified with respect to anthropogenic and geogenic pollutions from Equation II using the Equation I, $$Pb(\%)_{anthr.} = \frac{(^{206}Pb/^{207}Pb)_{geogenic} - (^{206}Pb/^{207}Pb)_{sample}}{(^{206}Pb/^{207}Pb)_{geogenic} - (^{206}Pb/^{207}Pb)_{anthr.}} \times 100 \quad \text{Equation II}$$

in which Pb (%)$_{anthr.}$ denotes the contribution ratio to the soil contamination by anthropogenic pollution, $(^{206}Pb/^{207}Pb)_{geogenic}$ denotes a Pb stable isotope value by geogenic pollution, $(^{206}Pb/^{207}Pb)_{anthr.}$ denotes a Pb stable isotope value by anthropogenic pollution, and $(^{206}Pb/^{207}Pb)_{sample}$ denotes a Pb stable isotope value of an analyte to be researched.

\* \* \* \* \*